(12) United States Patent
Selph et al.

(10) Patent No.: US 8,247,571 B2
(45) Date of Patent: Aug. 21, 2012

(54) PYRIDINIUM AND THIAZOLIUM CONJUGATES INCLUDING POLYETHYLENE GLYCOLS AND METHODS OF USING THE SAME

(75) Inventors: Jeffrey L. Selph, Cary, NC (US); Richard B. Klein, Cary, NC (US); John J. Partridge, Chapel Hill, NC (US)

(73) Assignee: Mycosol, Inc., Cary, NC (US)

( * ) Notice: Subject to any disclaimer, the term of this patent is extended or adjusted under 35 U.S.C. 154(b) by 471 days.

(21) Appl. No.: 12/093,015

(22) PCT Filed: Nov. 8, 2006

(86) PCT No.: PCT/US2006/043748
§ 371 (c)(1),
(2), (4) Date: Aug. 2, 2010

(87) PCT Pub. No.: WO2007/056556
PCT Pub. Date: May 18, 2007

(65) Prior Publication Data
US 2011/0053987 A1    Mar. 3, 2011

Related U.S. Application Data

(60) Provisional application No. 60/734,518, filed on Nov. 8, 2005, provisional application No. 60/773,366, filed on Feb. 13, 2006.

(51) Int. Cl.
C07D 401/00    (2006.01)
C07D 211/70    (2006.01)
A01N 43/40     (2006.01)

(52) U.S. Cl. .................. 546/276.4; 546/334; 514/343; 514/357

(58) Field of Classification Search ............... 546/276.4, 546/334; 514/343, 357
See application file for complete search history.

(56) References Cited

U.S. PATENT DOCUMENTS
3,075,975 A * 1/1963 Phillips et al. ............... 546/187
3,883,658 A   5/1975 Phillips et al.

FOREIGN PATENT DOCUMENTS
WO    WO 2004/078136 A2    9/2004

OTHER PUBLICATIONS
Notification of Transmittal of the International Search Report and the Written Opinion of the International Searching Authority, or the Declaration, corresponding to International Application No. PCT/US2006/043748 mailed May 23, 2007.

\* cited by examiner

*Primary Examiner* — Nizal Chandrakumar
(74) *Attorney, Agent, or Firm* — Myers Bigel Sibley & Sajovec, PA

(57) ABSTRACT

Pegylated pyridinium and thiazolium compounds and methods of their use in medicine, research, industry, agriculture and recreational activities are disclosed. The present invention also provides methods of controlling microbial growth and infection. Additionally, the present invention provides methods of controlling microbial infestations relating to industrial and agricultural uses. The present invention can also be used to control insects.

15 Claims, 4 Drawing Sheets

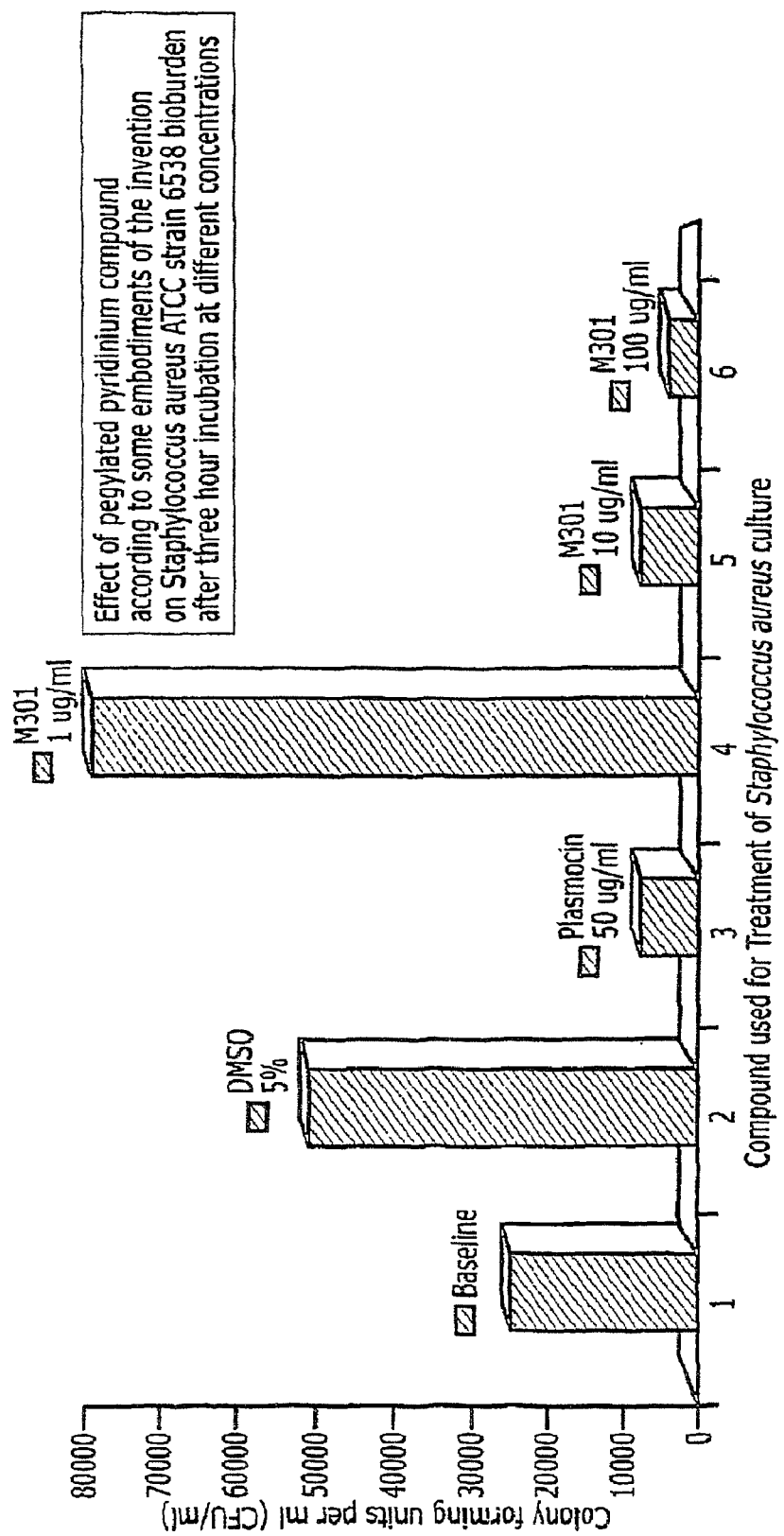

PYRIDINIUM AND THIAZOLIUM CONJUGATES INCLUDING POLYETHYLENE GLYCOLS AND METHODS OF USING THE SAME

RELATED APPLICATION INFORMATION

This application is a 35 U.S.C. §371 national phase application of International Application Serial No. PCT/US2006/043748, filed on Nov. 8, 2006, which claims the benefit of U.S. Provisional Patent Application Ser. No. 60/734,518, filed Nov. 8, 2005, and U.S. Provisional Patent Application Ser. No. 60/773,366 filed on Feb. 13, 2006. The disclosures of each of which are incorporated herein by reference in their entireties.

FIELD OF THE INVENTION

The present invention generally relates to conjugates of pyridinium and thiazolium compounds including polyalkylene glycols and methods of their use in medicine, research, industry, agriculture and recreational usage.

BACKGROUND OF THE INVENTION

Stilbazium iodide is a known anthelmintic which is reported to be effective against roundworms, threadworms, and whipworms. U.S. Pat. Nos. 3,075,975 and 3,085,935 discuss methods of eradicating infestations of parasitic nematodes inhabiting the intestinal tract.

The adhesion of circulating leukocytes to the vascular endothelium plays a role in the pathogenesis of inflammatory responses. Inflammatory, infectious and immune mediators can stimulate the adhesion process by increasing the adhesiveness of the leukocyte or the endothelial cell through the activation, up-regulation, or induction of various adhesion molecules on the cell surface.

Anti-inflammatory drugs currently available have limited efficacy, often with side effects. Monoclonal antibodies used experimentally for anti-adhesion therapies may have theoretical disadvantages for treatment of chronic diseases. Therefore, the discovery and development of small molecules that specifically block or inhibit the adhesive interactions of leukocytes and the endothelium is an attractive area of therapeutic intervention.

Additionally, there is a need for treating microorganisms such as fungi and/or bacteria using new compounds. Fungi include organisms such as slime molds, mushrooms, smuts, rusts, mildews, molds, stinkhorns, puffballs, truffles and yeasts. Molds constitute a large group of fungi that are a common trigger for allergies and affect crops, plants and food. Molds can exist as tiny particles called "mold spores" present in indoor and outdoor air. Molds may grow in environments that present moisture sources. Common molds include, but are not limited to, *Cladosporium, Penicillium, Aspergillus, Alternaria, Fusarium, Neurospora, Stachybotyrs* and *Mucor.*

Soil-borne and seed-borne fungal pathogens of plants are responsible for severe economic losses in the agricultural and horticultural industries worldwide. These pathogens cause plant diseases such as seed decay, root/foot rot, seedling blight and wilt. Such diseases commonly reduce emergence, plant vigor and yield potential. Severe disease infection can kill emerging seedlings of an entire plant population, and result in a total loss of crop yield.

Solutions to the recurring problem of plant pathogens have been explored for decades. As particular crops become more abundant, and the area of land allocated for agriculture expands, there is a need to employ more efficient and effective farming practices. As a result of increasing demand for crop production, farmers must often compromise their cultural practices by planting crops on sub-optimal land, or by increasing the frequency at which crops are planted in a specific location. In doing so, crop nutrients are depleted and specific crop pathogens, especially soil-borne or seed-borne pathogens, become more prevalent. Accordingly, it is increasingly difficult to sustain the health and productivity of a respective crop.

There also exists the need to control algae and alga-like euglena species, particularly using compounds that are more environmentally friendly and less toxic to humans, animals and aquatic species including vertebrates and invertebrates. Algae include alga-like euglena species and organisms such as pond scums, terrestrial algae, snow algae, seaweeds, freshwater and marine phytoplankton etc. Common algae include, but are not limited to bacillariophyta (diatoms), chlorophyta (green algae), chrysophyta (golden-brown algae), cryptophyta (cryptomonads), cyanobacteria (blue-green algae), dinophyta (dinoflagellates), euglenophyta (euglenoids), glaucophyta, phaeophyta (brown algae), tribophyta (yellow-green algae), prymnesiophyta (haptophytes) and rhodophyta (red algae).

Additionally, vast demands exist for compounds to control microorganisms in fields other than agriculture. These include the treatment of fabrics to prevent mildew and rot; to inhibit and kill bacterial growth; the treatment of surfaces and substrates to obtain antiseptic conditions for medical, industrial, food processing and household purposes; the treatment of wood for decking or building; the formulation of ink and paints to prevent mold growth and bacterial decomposition; the prevention and treatment of human and animal diseases; and on through an almost infinite spectrum of applications impacting our daily lives.

Further, there is a continuing need for new antibacterial agents. Although many compounds are known which are useful in the treatment of gram-positive and gram-negative bacterial infections as well as other microbial infections, the widespread use of such compounds continues to give rise to resistant strains of microorganisms, i.e., strains of microorganisms against which a particular antibiotic or group of antibiotics, and chemical compositions which was previously effective, is no longer useful. Also, known antibiotics and chemical compositions may be effective against only certain strains of microorganisms or have limited activity against either gram-positive or gram-negative, aerobic or anaerobic organisms.

Accordingly, there is a need for new compounds and/or methods of combating microorganisms in medical, industrial, agricultural and recreational uses.

SUMMARY OF THE INVENTION

The present invention provides conjugates of pyridinium and thiazolium compounds including polyalkylene glycols and methods of their use in medicine, such as in the prophylaxis and treatment of inflammatory conditions, allergic conditions, infectious conditions, as well as immune disorders.

The present invention also provides methods of controlling algae, fungi, protozoans and/or bacteria, such as controlling algal, fungal, protozoal or bacterial infestations relating to industrial and agricultural uses. The present invention further provides conjugates that may be used to control insects.

In some embodiments, the present invention relates to methods of making and compositions including stilbazium compounds conjugated to polyalkylene glycols. In some embodiments, the polyalkylene glycol is polyethylene glycol. In other embodiments, the polyalkylene glycols are methoxy-polyethylene glycols, ethoxy-polyethylene glycols or acetyloxy-polyethylene glycols.

In other embodiments, the present invention provides a compound having the following structure:

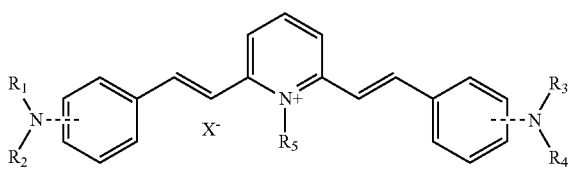

I or a solvate thereof, wherein
the compound is in an E, E configuration;
$NR_1R_2$ and $NR_3R_4$ are in the ortho, meta or para positions;
$X^-$ is an anionic salt;
$R_1$, $R_2$, $R_3$, or $R_4$ are the same or different and independently selected from the group consisting of $C_{1-10}$ alkyl (linear or branched) and alkenes (linear or branched), or wherein $R_1$ and $R_2$ or $R_3$ and $R_4$ taken together with the nitrogen atom to which they are attached form pyrrolidino or piperidino rings; and
$R_5$ is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy. The amino moieties on the aromatic rings can be in either the ortho, meta or para position.

In some embodiments, the compounds of the present invention include pegylated stilbazium chlorides, bromides, iodides, methanesulfonates (mesylates), p-toluenesulfonates (tosylates), benzenesulfonates (besylates), m-nitrobenzenesulfonates (nosylates), lauryl sulfates, p-aminobenzoates and the like.

In some embodiments, the present invention relates to methods of making and compositions including thiazolium compounds conjugated to polyalkylene glycols. In some embodiments, the polyalkylene glycol is polyethylene glycol. In other embodiments, the polyalkylene glycols are methoxy-polyethylene glycols, ethoxy-polyethylene glycols or acetyloxy-polyethylene glycols.

In some embodiments, the present invention provides a compound having the following structure:

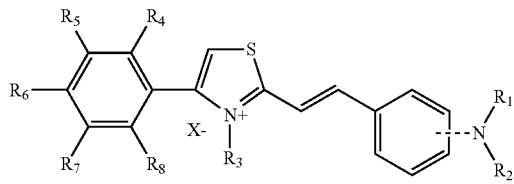

or a solvate thereof wherein the compound is substantially in the E, E configuration, or the compound can also be in the E, Z or Z, Z configuration and wherein:
the amino moieties can be in either the ortho, meta or para positions;

the anion $X^-$ can be fluoride, chloride, bromide, iodide, halide, methanesulfonate (mesylate), benzenesulfonate (besylate), p-toluenesulfonate(tosylate), napthylate, m-nitrobenzenesulfonate (nosylate), para-aminobenzoate, latnyl sulfate, 2,4-dihydroxy benzophenone, or 2-(2-hydroxy-5'-methylphenyl)benzotriazole;
$R_1$ and $R_2$ can be the same or different and are independently selected from the group consisting of methyl, ethyl, $C_{1-10}$ alkyl (linear or branched) and alkenes (linear or branched), or wherein $R_1$ and $R_2$ may be taken together with the nitrogen atom to which they are attached form pyrrolidino or piperidino rings;
$R_3$ can be a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy;
$R_4$ through $R_8$ can be the same or different and can be selected from the group consisting of hydrogen, $C_{1-10}$ alkyl (linear or branched), representative examples of alkyl including, but not limited to, n-propyl, i-propyl, n-butyl, i-butyl, alkenes (linear or branched), alkynes, substituted and unsubstituted aryl moieties and substituted and unsubstituted benzyl moieties, hydroxy, alkoxy, $SCH_3$, ($C_1$-$C_3$) alkylthio, SH, ($C_1$-$C_3$) haloalkoxy, ($C_1$-$C_3$) perhaloalkoxy, $NH_2$, NH(lower N(lower alkyl)$_2$, halogen, ($C_1$-$C_3$) haloalkyl, ($C_1$-$C_3$) perhaloalkyl, —$CF_3$, —$CH_2CF_3$, —$CF_2CF_3$, —CN, —NC, —OCN, —SCN, —NO, —$NO_2$, —$N_3$, —S(O) (lower alkyl), —S(O) (aryl), —S(O)$_2$ (lower alkyl), —S(O)$_2$ (aryl), S(O)$_2$ (alkoxyl), —S(O)$_2$(aryloxy), —S(O)$NH_2$; —S(O)$_2$NH-lower alkyl, —S(O)$_2$NH-aryl, —S(O)$_2$N-(lower alkyl)$_2$, —S(O)$_2$N-(aryl)$_2$, —C(O)$R_a$, —C(O)$OR_a$, —C(O)$NR_aR_b$, —C(NH)$NR_aR_b$, —OC(O)$R_a$, —SC(O)$R_a$, —OC(O)$OR_a$, —SC(O)$OR_a$, —OC(O)$NR_aR_b$, —SC(O)$NR_aR_b$, —OC(NH)$NR_aR_b$, —SC(NH)$NR_aR_b$, —[NHC(O)]$_n$$R_a$, —[NHC(O)]$_n$$OR_a$, —[NHC(O)]$_n$$NR_aR_b$ and —[NHC(NH)]$_n$$NR_aR_b$, wherein n is an integer from 1 to 5, and wherein $R_a$ and $R_b$ can be the same or different and are independently selected from the group consisting of hydrogen, halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro; mercapto, sulfinyl, sulfonyl and sulfonamide; and any of $R_4$ through $R_8$ together can form a fused ring.

In further embodiments, the present invention provides methods of controlling insects including administering a composition including the compounds described herein or a solvate thereof.

In still other embodiments, the present invention provides methods of treating inflammatory disorders, allergic conditions, infections and immune disorders including administering the compounds and/or compositions described herein. The present invention also provides methods of controlling fungi and/or bacteria including administering a composition including the compounds described herein or a solvate thereof.

In still other embodiments, the present invention provides encapsulated compositions that are stabilized against environmental degradation.

In some embodiments, the present invention provides microcapsules having an ultraviolet absorber and an organic solvent enclosed therein, which have a capsule wall film of synthetic resin and mean particle size of 0.1 to 3 μm.

In still other embodiments, the present invention provides methods of treating a vast array of microorganisms.

Embodiments of the present invention also provide compounds having staining capabilities for staining cells, analytes, nucleic acids and/or microorganisms.

Embodiments of the present invention further provide kits for staining cells, analytes, nucleic acids and/or microorganisms.

In further embodiments, compounds of the present invention can be used in the preparation of a medicament, industrial product or agricultural product.

BRIEF DESCRIPTION OF THE DRAWINGS

FIG. 4 shows a graph depicting the effect of a pegylated pyridinium compound according to some embodiments of the present invention on *Staphylococcus aureus*.

DETAILED DESCRIPTION

Figure 1:
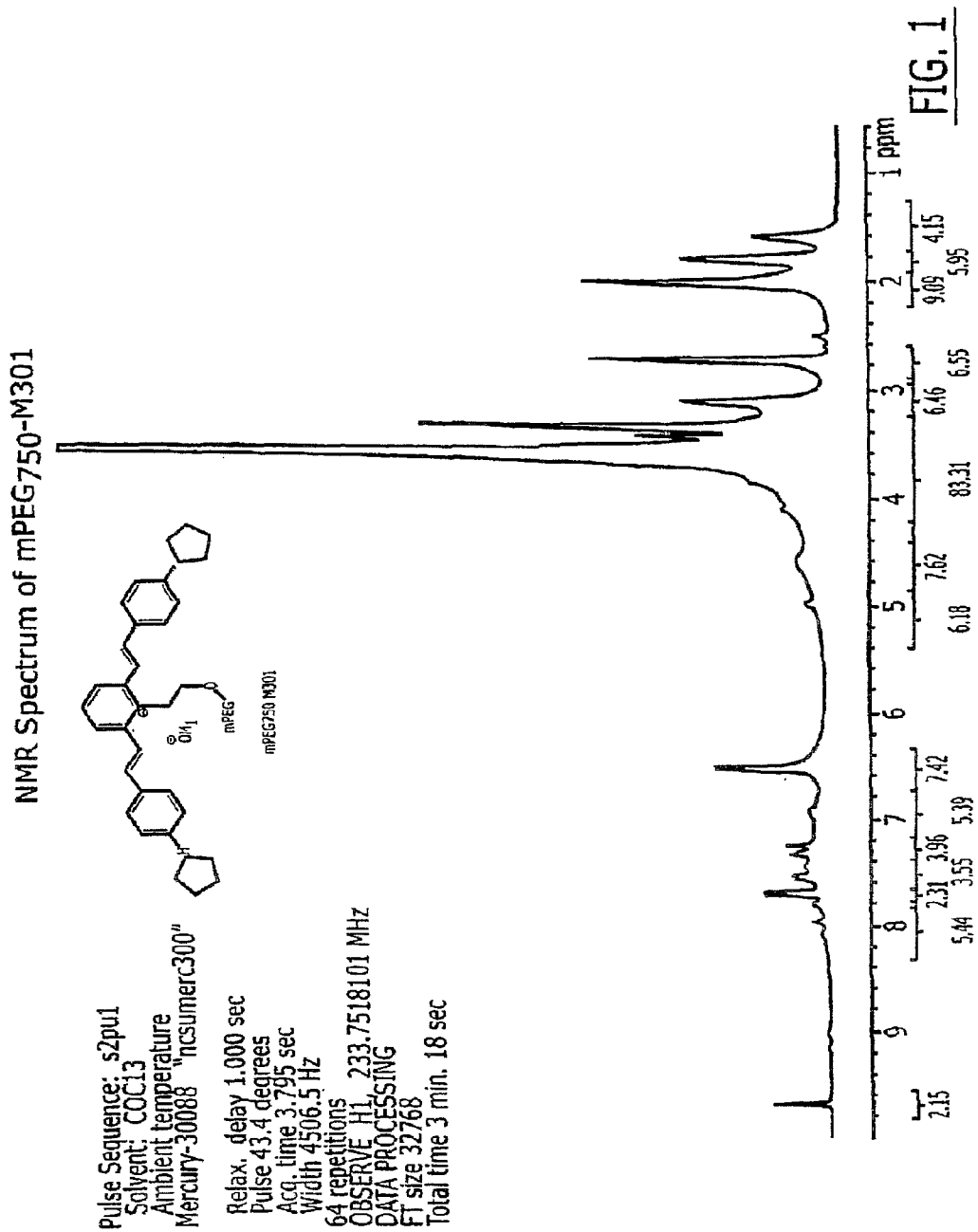
FIG. 1 shows a nuclear magnetic resonance (NMR) spectrum of a pegylated pyridinium compound according to some embodiments of the present invention.

The foregoing and other aspects of the present invention will now be described in more detail with respect to other embodiments described herein. It should be appreciated that the invention can be embodied in different fours and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular fowls "a", "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, 0.1% or even 0.01% of the specified amount. Unless otherwise defined, all terms, including technical and scientific terms used in the description, have the same meaning as commonly understood by one of ordinary skill in the art to which this invention belongs.

All publications, patent applications, patents and other references cited herein are incorporated by reference in their entireties for the teachings relevant to the sentence and/or paragraph in which the reference is presented.

As used herein, the term "microbe" or "microbial" refers to microscopic organisms that can exist as a single cell or cell clusters.

As used herein, the term "eliminating" refers to complete cessation of the specified activity.

As used herein, the term "reducing" or "reduce" refers to a decrease or diminishment in the specified activity of at least about 10%, 25%, 35%, 40%, 50%, 60%, 75%, 80%, 90%, 95% or more. In some embodiments, the reduction results in little or essentially no detectable activity (at most, an insignificant amount, e.g., less than about 10% or even 5%).

As used herein, the term "retarding the growth" or "retardation of growth" refers to reducing, delaying and/or hindering activity contributing to the growth of the microorganism.

As used herein, the term "effective amount" refers to an amount of a compound or composition that is sufficient to produce the desired effect, which can be a therapeutic or agricultural effect. The effective amount will vary with the application for which the compound or composition is being employed, the microorganism and/or the age and physical condition of the subject, the severity of the condition, the duration of the treatment, the nature of any concurrent treatment, the pharmaceutically or agriculturally acceptable carrier used, and like factors within the knowledge and expertise of those skilled in the art. An appropriate "effective amount" in any individual case can be determined by one of ordinary skill in the art by reference to the pertinent texts and literature and/or by using routine experimentation. (See, for example for pharmaceutical applications, Remington, *The Science And Practice of Pharmacy* (9$^{th}$ Ed. 1995).

As used herein, the term "treat" or "treatment" refers to an action resulting in a reduction in the severity of the subject's condition or at least wherein the condition is partially improved or ameliorated and/or that some alleviation, mitigation or decrease in at least one clinical symptom (or agricultural index for plants or comparable measure for industrial products) is achieved and/or there is a delay in the progression of the condition and/or prevention or delay of the onset of the condition. Thus, the term "treat" refers to both prophylactic and therapeutic treatment regimes.

Pyridinium and Thiazolium Compounds

The present invention relates to pyridinium and thiazole compounds, analogs, homologs and derivatives, processes for their preparation, methods of their use and compositions including the same.

Stilbazium iodide is a known antihelmintic, which is reported to be effective against roundworms, threadworms, and whipworms. U.S. Pat. Nos. 3,075,975 and 3,085,935 discuss methods of eradicating infestations of parasitic nematodes inhabiting the intestinal tract.

Embodiments of the present invention include compounds having the following structure:

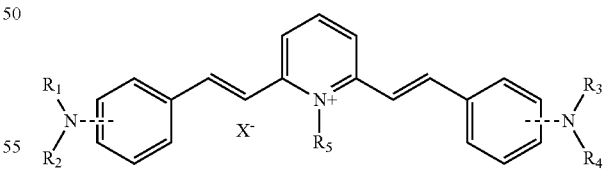

or a solvate thereof, wherein X⁻ is an anionic salt, wherein $R_1$, $R_2$, $R_3$, or $R_4$ are the same or different and independently selected from the group consisting of methyl, ethyl, $C_{1-10}$ alkyl (linear or branched) and alkenes (linear or branched), or wherein when $R_1$ and $R_2$ or when $R_3$ and $R_4$ are taken together with the nitrogen atom to which they are attached, form pyrrolidino or piperidino rings. X⁻ can be selected from the group including fluoride, chloride, bromide, iodide, halide, methanesulfonate(mesylate), benzenesulfonate(besylate), p-toluenesulfonate (tosylate), napthylate, m-nitrobenzenesulfoinate(nosylate), para-aminobenzoate, lauryl sulfate, 2,4-dihydroxy benzophenone or 2-(2-hydroxy-5'-methylphenyl)benzotriazole. $R_5$ is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy. The amino moieties on the aromatic rings can be in either the ortho, meta or para position.

The compounds of the present invention are capable of existing as geometric isomers. All such isomers, individually and as mixtures, are included within the scope of the present invention for their industrial uses. The E,E isomer is one configuration of the invention, and both the cisoid and transoid 2,6-conformations of the E,E-configuration are possible. Additionally, ortho conformation of the structure can be formed in addition to the para and meta structures described herein. The ortho conformation structure can include the same salts and moieties as described herein.

Another embodiment of the present invention includes a compound having the following structure:

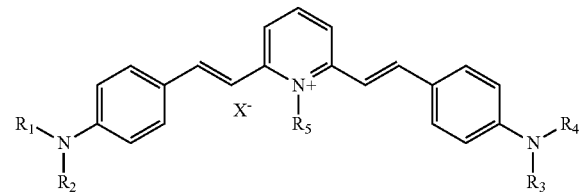

or a solvate thereof, wherein X⁻ is an anionic salt, wherein $R_1$, $R_2$, $R_3$, or $R_4$ are the same or different and are independently selected from the group consisting of methyl, ethyl, $C_{1-10}$ alkyl (linear or branched) and alkenes (linear or branched), or wherein when $R_1$ and $R_2$ or when $R_3$ and $R_4$ are taken together with the nitrogen atom to which they are attached, they form pyrrolidino or piperidino rings. $R_5$ is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy. The amino moieties on the aromatic rings can be in either the ortho, meta or para position.

The anion X⁻ can be fluoride, chloride, bromide, iodide, halide, mesylate, tosylate, napthylate, nosylate, para-aminobenzoate, lauryl sulfate, 2,4-dihydroxy benzophenone, 2-(2-hydroxy-5'-methylphenyl)benzotriazole, or benzenesulfonate(besylate). In some embodiments, the PEGylated compound is 2,6,-bis(p-pyrrolidinostyryl)pyridinium methoxy(polyethyleneoxy)-ethiodide, also known as 2,6-bis-[2-[4-(N-pyrrolidino)phenyl]vinyl]-1-[methoxy(polyethyleneoxy)$_{n-1}$]-ethyl pyridinium iodide or "mPEG-1000-stilbazium iodide".

Alternatively, in some embodiments, the $NR_1R_2$ and $NR_3R_4$ moieties can be in various positions as evidenced below. For example, in one embodiment, the $NR_1R_2$ moiety is in one meta position:

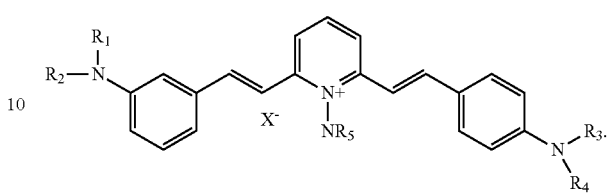

In another embodiment, the $NR_1R_2$ and $NR_3R_4$ moieties are present in both meta positions:

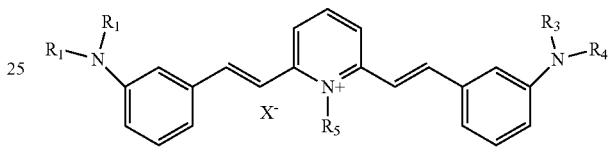

wherein X⁻ may be an anionic salt, $R_1$, $R_2$, $R_3$, or $R_4$ are the same or different and are independently selected from the group consisting of methyl, ethyl, $C_{1-10}$ alkyl (linear or branched) and alkenes (linear or branched), or wherein when $R_1$ and $R_2$ or when $R_3$ and $R_4$ are taken together with the nitrogen atom to which they are attached, they form pyrrolidino or piperidino rings. $R_5$ is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy. The amino moieties on the aromatic rings can be in either the ortho, meta or para position.

According to some embodiments of the present invention, the compounds can be 2,6-bis-[2-[4-(N-pyrrolidino)phenyl]vinyl]-1-[methoxy(polyethyleneoxy)$_{n-1}$]-ethyl pyridinium p-toluenesulfonate (mPEG350-stilbazium tosylate), wherein n is from 5-8 and X is tosyl (OT). In other embodiments, the compounds can be 2,6-bis-[2-[4-(N-pyrrolidino)phenyl]vinyl]-1-[methoxy(polyethyleneoxy)$_{n-1}$]-ethyl pyridinium methanesulfonate (mPEG750-stilbazium mesylate), wherein n is from 15 to 17 and X is methanesulfonyl (OMs). In some embodiments, the compounds can be 2,6-bis-[2-[4-(N-pyrrolidino)phenyl]vinyl]-1-[methoxy(polyethyleneoxy)$_{n-1}$]-ethyl pyridinium chloride (mPEG1000-stilbazium chloride), wherein n is from 19 to 24 and X is Cl. In other embodiments, the compounds can be 2,6-bis-[2-[4-(N,N-dimethylamino)phenyl]vinyl]-1-[methoxy(polyethyleneoxy)$_{n-1}$]-ethyl pyridinium p-toluenesulfonate, wherein n is from 6 to 8 and X is tosyl (OTs). In still other embodiments, the compounds can be 2,6-bis-[2-[4-(N,N-dimethylamino)phenyl]vinyl]-1-[methoxy(polyethyleneoxy)$_{n-1}$]-ethyl pyridinium methanesulfonate, wherein n is from 15 to 17 range and X is methanesulfonyl (OMs). In other embodiments, the compounds can be 2,6-bis-[2-[4-(N,N-dimethylamino)phenyl]vinyl]-1-[methoxy(polyethyleneoxy)$_{n-1}$]-ethyl pyridinium chloride, wherein n is from 19 to 24 and X is Cl.

Additionally, the present invention can include compounds having the following structure:

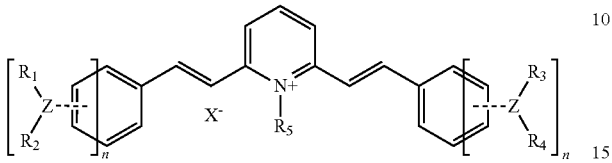

or a solvate thereof, wherein n is a number from 1 to 5, wherein 2 can be present at multiple positions on the phenyl ring and is selected from the group consisting of C, N, O, S and halogen, wherein X$^-$ is an anionic salt, wherein $R_1$, $R_2$, $R_3$, or $R_4$ are independently not present or are the same or different and selected from the group consisting of hydrogen, methyl, ethyl, $C_{1-10}$ alkyl (linear or branched), alkenes (linear or branched), nitriles, benzenes, pyridines, benzothiophenes, trifluoroalkyls, dffluoroalkyls, substituted and unsubstituted aryl moieties and substituted and unsubstituted benzyl moieties, or wherein when $R_1$ and $R_2$ or when $R_3$ and $R_4$ are taken together with the nitrogen atom to which they are attached, they form pyrrolidino or piperidino rings. The anion X$^-$ can be fluoride, chloride, bromide, iodide, halide, methanesulfonate(mesylate), benzenesulfonate(besylate), p-toluenesulfonate (tosylate), napthylate, m-nitrobenzenesulfonate (nosylate), para-aminobenzoate, lauryl sulfate, 2,4-dihydroxy benzophenone, or 2-(2-hydroxy-5'-methylphenyl) benzotriazole. $R_5$ is a polyalkylene glycol moiety including a $C_{1-5}$ alkyl (linear or branched) substituted polyethylene glycol, a $C_{2-5}$ alkene (linear or branched) substituted polyethylene glycol, a $C_{2-5}$ alkyne substituted polyethylene glycol. The end-terminals of these polyethylene glycol moieties can be hydroxy, methoxy, ethoxy and acetyloxy. The amino moieties on the aromatic rings can be in either the ortho, meta or para position.

Figure 2:
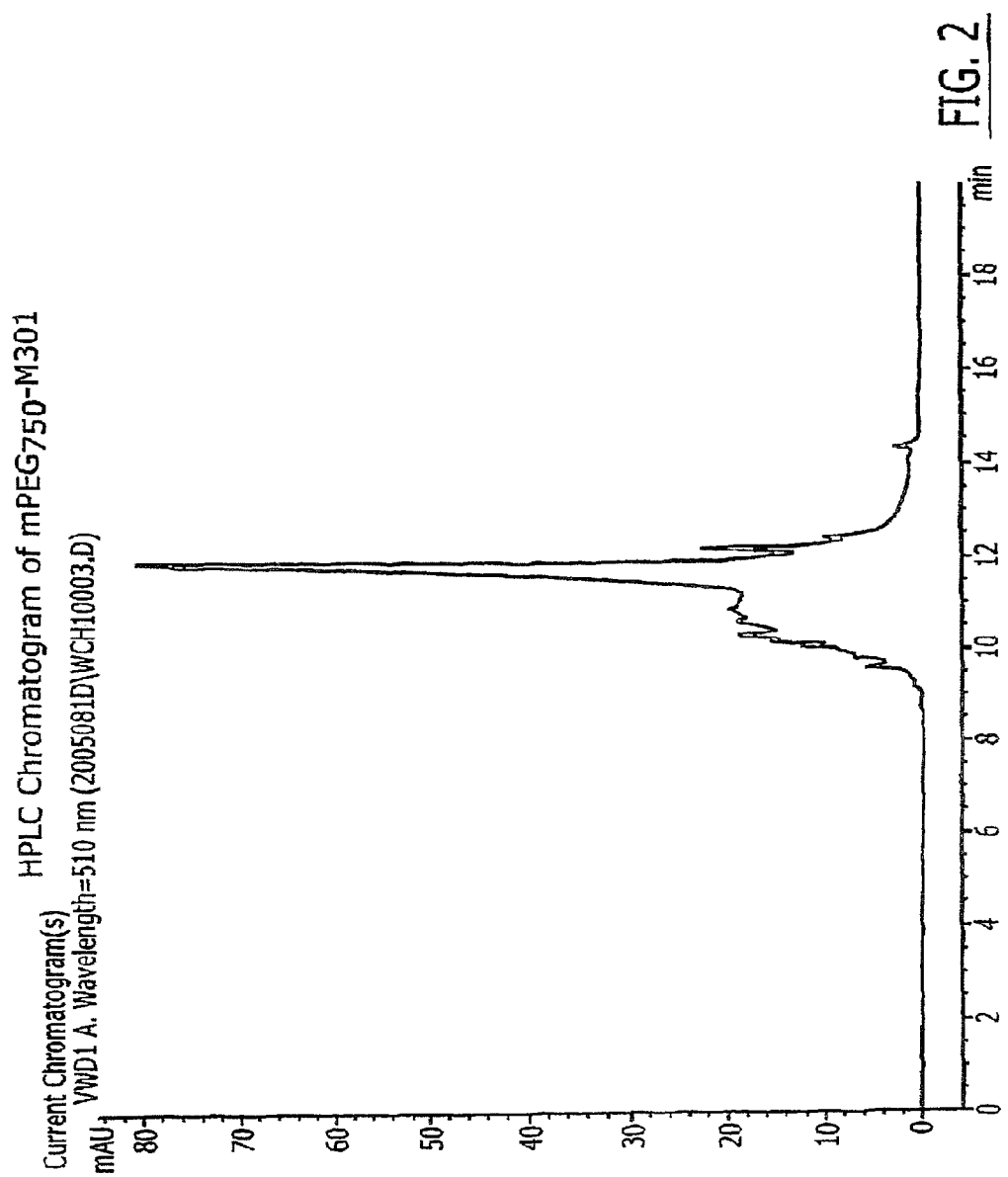
FIG. 2 shows a high performance liquid chromatography (HPLC) chromatogram of a pegylated pyridinium compound according to some embodiments of the present invention.
Figure 3:
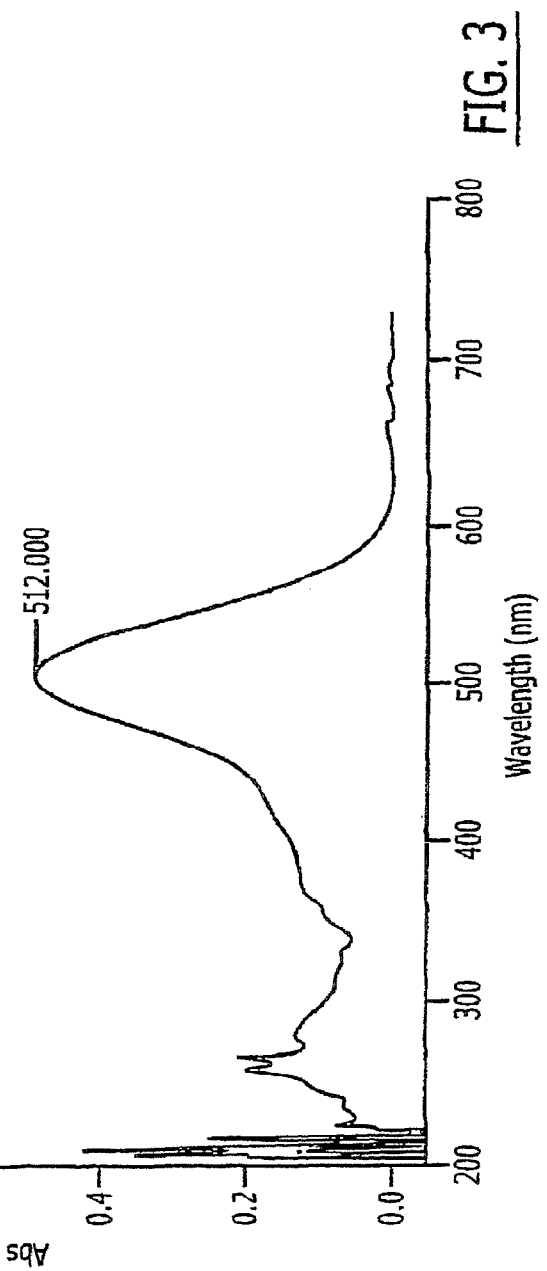
FIG. 3 shows a UV-visible spectrum of a pegylated pyridinium compound according to some embodiments of the present invention.

FIGS. 1 through 4 illustrate various combinations of the compounds that may be formed according to the present invention. These compounds can be in the E,E configuration and can be used for any of the uses disclosed in the present application.

Parent compounds according to the invention can be made according to any suitable method of organic chemistry. More specifically, compounds described above can be prepared as outlined in U.S. Pat. No. 3,085,935.

Additionally, embodiments of the present invention may include native compounds produced by a synthesis that includes preparing the compounds by condensation of two equivalents of an aldehyde as shown below

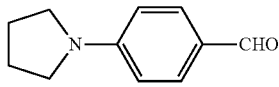

with a quaternary ammonium salt of 2,6-lutidine

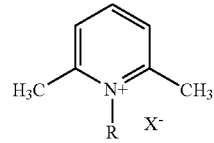

The condensation may be performed in a lower alcohol with a catalyst such as a secondary amine (e.g., piperidine). When the anion X$^-$ in the above formula is an iodide ion (corresponding to an alkiodide salt of lutidine), the condensation product is relatively insoluble and precipitates in the course of the reaction. The reaction yield of the final product can be nearly quantitative. At least three times the amount of catalyst as stated in U.S. Pat. No. 3,085,935 can be used. Other methods may be used to produce the compound and both more or less catalyst may be employed to produce the resulting compounds.

For the above reactions described above, R is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy.

Furthermore, it may be desirable to convert the iodide salt to the chloride salt. This conversion can be accomplished by size exclusion (molecular sieve) chromatography, eluted and equilibrated with a suitable solvent containing an excess of ammonium chloride. The column effluent, containing the chloride salt can be obtained by evaporation of the solvent, along with the ammonium iodide by-product. The resulting product should be substantially free of the iodide salt. Alternatively, an alkiochloride salt of 2,6-lutidine can be reacted with an aldehyde in the presence of a secondary amine (e.g., piperidine) to give the chloride salt of the compound directly.

Alternatively, the compound can be prepared by dissolving 2,6-lutidine ethiodide in methanol, followed by bubbling anhydrous HCl (220 grams) slowly into the solution. An ice/H$_2$O bath can be used to keep the reaction below 30° C. After all the HCl has been added, the reaction is stirred overnight at room temperature. After stirring, the reaction should be concentrated to near dry and re-diluted with 1000 mL of fresh methanol. The ethiodide can be converted to the desired ethochloride by, bubbling anhydrous HCl into the mixture. After stirring 10 minutes, the reaction is concentrated to dry on a rotovap, and placed on hi-vacuum manifold for final drying overnight.

The chloride salt can have an increased stability as compared to the iodide salt. Other methods known in the art may be utilized to convert the salts to UV blocker salts or surfactant salts. Other anionic salts may include:

Formula A-PEGylated stilbazium p-aminobenzoate salts

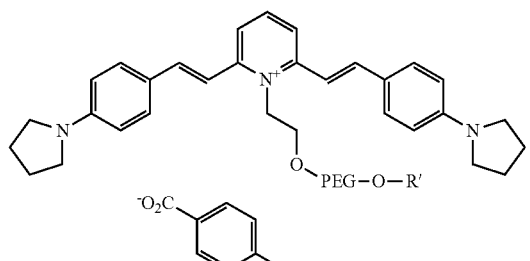

R' is H, CH₃, C₂H₅ and CH₃CO

Formula B-PEGylated stilbazium dodecyl sulfate salt (PEGylated stilbazium lauryl sulfate salts)

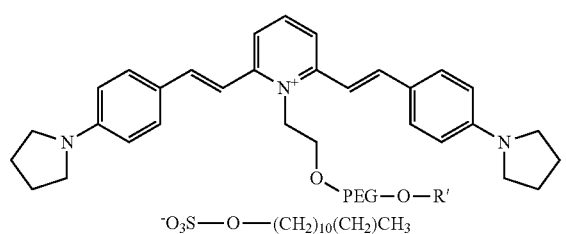

R' is H, CH₃, C₂H₅ and CH₃CO

Additional anionic "salts" may be produced from substituted benzophenones such as 2,4-dihydroxy benzophenone, and substituted benzotriazoles, such as 2-(2-hydroxy-5'-methylphenyl)benzotriazole.

The anionic salts may include an ultraviolet blocker or a surfactant as an additional ingredient. As used herein "ultraviolet blocker" refers to all "photosensitive materials" which refers to all compositions and materials designed to block and/or absorb ultraviolet light. This term also refers to all photoprotective and photoresistant agents. Accordingly, X⁻ as recited herein can include an ultraviolet blocker, an ultraviolet absorber or a surfactant.

Further embodiments of the present invention include thiazolium compounds. In some embodiments, the compounds have the following structure:

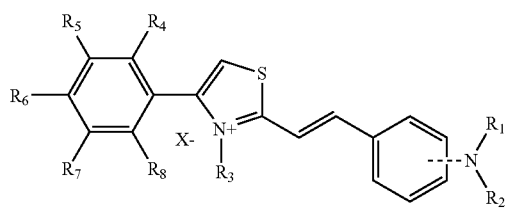

or a solvate thereof wherein the compound is substantially in the E, E configuration, or the compound can also be in the E,Z or Z,Z configuration. The amino moieties can be in either the ortho, meta or para positions. The anion X⁻ can be fluoride, chloride, bromide, iodide, halide, methanesulfonate(mesylate), benzenesulfonate(besylate), p-toluenesulfonate (tosylate), napthylate, m-nitrobenzenesulfonate(nosylate), para-aminobenzoate, lauryl sulfate, 2,4-dihydroxy benzophenone, or 2-(2-hydroxy-5'-methylphenyl)benzotriazole. $R_1$ and $R_2$ are the same or different and are independently selected from the group consisting of methyl, ethyl, $C_{1-10}$ alkyl (linear or branched) and alkenes (linear or branched), or wherein $R_1$ and $R_2$ may be taken together with the nitrogen atom to which they are attached form pyrrolidino or piperidino rings. $R_3$ is a polyalkylene glycol moiety including a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol. The end-terminals of these polyethylene glycol moieties can be hydroxy, methoxy, ethoxy and acetyloxy. $R_4$ through $R_8$ are the same or different and may be selected from the group consisting of hydrogen, $C_{1-10}$ alkyl (linear or branched), representative examples of alkyl including, but not limited to, n-propyl, i-propyl, n-butyl, i-butyl, alkenes (linear or branched), alkynes, substituted and unsubstituted aryl moieties and substituted and unsubstituted benzyl moieties, hydroxy, alkoxy, $SCH_3$, $(C_1-C_3)$ alkylthio, $SH$, $(C_1-C_3)$ haloalkoxy, $(C_1-C_3)$ perhaloalkoxy, $NH_2$, NH(lower alkyl), N(lower alkyl)$_2$, halogen, $(C_1-C_3)$ haloalkyl, $(C_1-C_3)$ perhaloalkyl, —$CF_3$, —$CH_2CF_3$, —$CF_2CF_3$, —CN, —NC, —OCN, —SCN, —NO, —$NO_2$, —$N_3$, —S(O) (lower alkyl), —S(O) (aryl), —S(O)$_2$ (lower alkyl), —S(O)$_2$ (aryl), S(O)$_2$ (alkoxyl), —S(O)$_2$(aryloxy), —S(O)$NH_2$; —S(O)$_2$NH-lower alkyl, —S(O)$_2$NH-aryl, —S(O)$_2$N-(lower alkyl)$_2$, —S(O)$_2$N-(aryl)$_2$, —C(O)$R_a$, —C(O)$OR_a$, —C(O)$NR_aR_b$, —C(NH)$NR_aR_b$, —OC(O)$R_a$, —SC(O)$R_a$, —OC(O)$OR_a$, —SC(O)$OR_a$, —OC(O)$NR_aR_b$, —SC(O)$NR_aR_b$, —OC(NH)$NR_aR_b$, —SC(NH)$NR_aR_b$, —[NHC(O)]$_nR_a$, —[NHC(O)]$_nOR_a$, —[NHC(O)]$_n$ $NR_aR_b$ and —[NHC(NH)]$_n$ $NR_aR_b$, wherein n is an integer from 1 to 5, and wherein $R_a$ and $R_b$ can be the same or different and are independently selected from the group consisting of hydrogen, halogen, trifluoromethyl, alkyl, substituted alkyl, cycloalkyl, substituted cycloalkyl, a heterocyclic group, a substituted heterocyclic group, aryl, substituted aryl, heteroaryl, substituted heteroaryl, hydroxy, alkoxy, aryloxy, amino, formyl, acyl, carboxy, carboxyalkyl, carboxyaryl, amido, carbamoyl, guanidino, ureido, amidino, cyano, nitro, mercapto, sulfinyl, sulfonyl and sulfonamide, and any of $R_4$ through $R_8$ together can form a fused ring.

According to some embodiments of the present invention, a suitable thiazolium compound of the present invention can be pegylated at at least four sites and/or can be PEGylated in many differing PEG lengths and molecular weights. In some embodiments, the PEG moiety is $PEG_{200}$ through $PEG_{5000}$.

In some embodiments, the compounds have the following structure:

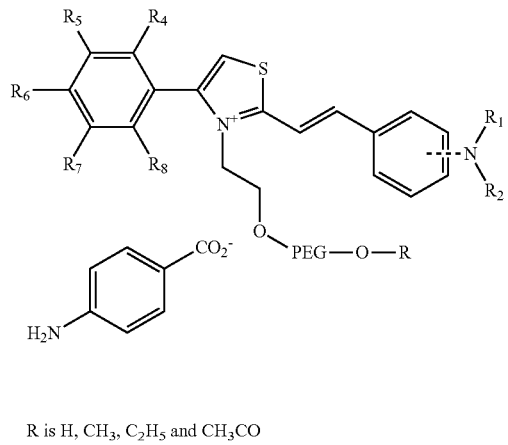

R is H, CH₃, C₂H₅ and CH₃CO

In further embodiments, the compounds have the following structure:

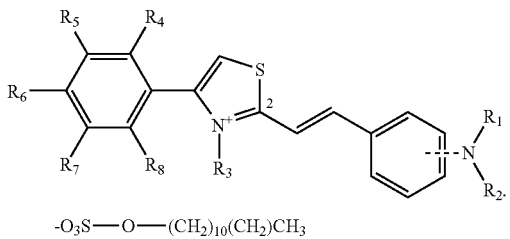

-O₃S—O—(CH₂)₁₀(CH₂)CH₃

As shown below in the Scheme 1, typically, commercially available substituted or unsubstituted phenyl methyl ketones (1) are reacted with bromine in a non-polar solvent to produce the corresponding phenacyl bromides (2). Reaction of the reactive alpha-bromo ketones (2) with commercially available thioacetamide (3) in an protic solvent such as methanol with heat afforded the 2-methyl-4-phenylthiazoles (4). N-Alkylation of thiazoles (4) with PEGylated alkyl halides such as MeO-PEG1000-Cl (5, Biolink Life Sciences, Inc., Cary, N.C. BLS-106-1000) in aprotic solvents such as dimethylformamide and heat readily formed the corresponding PEGylated products (6). Reaction of these thiazolium halides (6) with (N,N'-disubstituted)amino benzaldehydes (7) in a protic solvent such as methanol with a basic catalyst such as piperidine and heat then produces the desired 2-(N,N'-dialkylaminostyryl)-3-(PEGylated)alkyl-4-phenylthiazoliilm halides (8). This synthetic scheme can be carried out in accordance with procedures and modifications known to those skilled in the art such as those described in U.S. Pat. Nos. 3,641,012; 3,851,060 and 3,883,658.

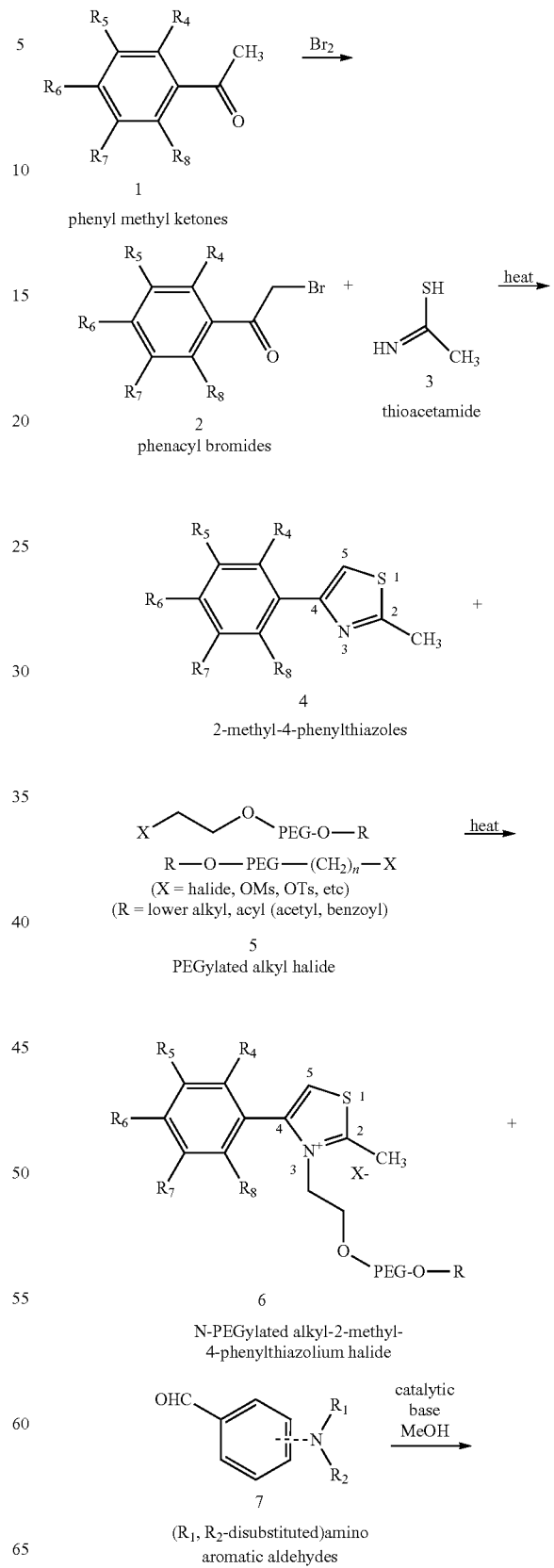

-continued

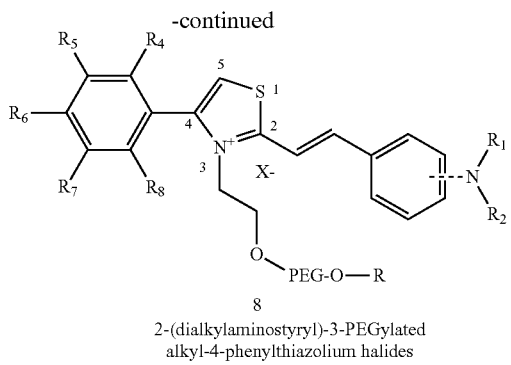

8
2-(dialkylaminostyryl)-3-PEGylated
alkyl-4-phenylthiazolium halides

PEGylation

In general, attachment of polyalkylene moieties as described herein can be employed to reduce immunogenicity and/or extend the half-life of the native compounds discussed herein. Any conventional PEGylation method can be employed, provided that the PEGylated agent retains pharmaceutical activity. See also Schacht, E. H. et al. *Poly(ethylene glycol) Chemistry and Biological Applications*, American Chemical Society, San Francisco, Calif. 297-315 (1997).

Polyalkylene glycol is a biocompatible polymer where, as used herein, polyalkylene glycol refers to straight or branched polyalkylene glycol polymers such as polyethylene glycol, polypropylene glycol, and polybutylene glycol, and further includes the monoalkylether of the polyalkylene glycol. In some embodiments of the present invention, the polyalkylene glycol polymer is a lower alkyl polyalkylene glycol moiety such as a polyethylene glycol moiety (PEG), a polypropylene glycol moiety, or a polybutylene glycol moiety. PEG has the formula $HO(CH2CH2O)_nH$, where n can range from about 1 to about 4000 or more. In some embodiments, n is 1 to 100, and in other embodiments, n is 5 to 30. PEG can range from average molecular weight of about 90 to about 180,000 or more. For example, an average molecular weight of about 300 can correspond to n is 5-6, an average molecular weight of about 2,300 can correspond to n is 50, an average molecular weight of about 13,300 can correspond to n is 300 and an average molecular weight of about 22,000 can correspond to n is 500. In some embodiments, the PEG moiety can be linear or branched. In further embodiments, PEG can be attached to groups such as hydroxyl, alkyl, aryl, acyl or ester. In some embodiments, PEG can be an alkoxy PEG, such as methoxy-PEG (or mPEG), where one terminus is a relatively inert alkoxy group, while the other terminus is a hydroxyl group.

PEG moieties are well known in the art and can be synthesized or are commercially available products that can be readily obtained. See, for example, http://www.biolinkonline.com/MPEG%20CATALOG.pdf According to some embodiments of the present invention, the pegylated compounds of the present invention can be water soluble, soluble in isopropyl alcohol (IPA), ethanol (EtOH), dimethyl sulfoxide (DMSO) and methanol (MeOH), less sensitive to UV light than a non-pegylated counterpart and/or economical to synthesize.

Pyridinium compounds suitable for PEGylation include, but are not limited to those described herein. Moreover, suitable pyridinium compounds include those described in U.S. patent application Ser. No. 10/792,339, filed Mar. 3, 2004, U.S. application Ser. No. 10/792,495, filed Mar. 3, 2004, and U.S. application Ser. No. 10/792,496, filed Mar. 3, 2004. A suitable pyridinium compound of the present invention can be pegylated at at least four sites (the 1-, 3-, 4- and 5-positions on the central pyridinium core) and/or can be PEGylated in many differing PEG lengths and molecular weights. In some embodiments, the PEG moiety is $PEG_{200}$ through $PEG_{5000}$.

Thiazolium compounds suitable for PEGylation include, but are not limited to, those described herein. Moreover, suitable thiazolium compounds include those described in published PCT application WO 2006/065942. A suitable thiazolium compound of the present invention can be pegylated at at least four sites and/$_o$r can be PEGylated in many differing PEG lengths and molecular weights. In some embodiments, the PEG moiety, is $PEG_{200}$ through $PEG_{5000}$.

Pegylated compounds of the present invention can further exhibit improved solubility, enhanced bioavailability, improved stability, lower toxicity, decreased degradation and chemical sensitivities and/or increased conjugation potential to like molecules and other drug molecules.

Microorganisms and Microbial Infections

In addition to the microorganisms previously discussed, microorganisms that can be affected according to methods of the present invention include, but are not limited to, bacteria, mycobacteria, spirochetes, rickettsia, chlamydia, mycoplasma, algae, fungi, protozoans, viruses, and parasites. Accordingly, methods disclosed herein relate to bacterial, mycobacterial, spirochetal, rickettsial, chlamydial, mycoplasmal, algal, fungal, viral, and parasitic infections.

Further bacterial infections that can be treated using the active agents of the present invention can be caused by bacteria such as gram-negative bacteria. Examples of gram-negative bacteria include, but are not limited to, bacteria of the genera, *Salmonella, Escherichia, Klebsiella, Haemophilus, Pseudomonas, Proteus, Neisseria, Vibrio, Helicobacter, Brucella, Bordetella, Legionella, Campylobacter, Francisella, Pasteurella, Yersinia, Bartonella, Bacteroides, Streptobacillus, Spirillum* and *Shigella*. Further wore, bacterial infections that can be treated using the active agents of the present invention can be caused by gram-negative bacteria including, but not limited to, *Escherichia coli, Pseudomonas aeruginosa, Neisseria meningitides, Neisseria gonorrhoeae, Salmonella typhimurium, Salmonella entertidis, Klebsiella pneumoniae, Haemophilus influenzae, Haemophilus ducreyi, Proteus mirabilis, Vibro cholera, Helicobacter pylori, Brucella abortis, Brucella melitensis, Brucella suis, Bordetella pertussis, Bordetella parapertussis, Legionella pneumophila, Campylobacter fetus, Campylobacter jejuni, Francisella tularensis, Pasteurella multocida, Yersinia pestis, Bartonella bacilliformis, Bacteroides fragilis, Bartonella henselae, Streptobacillus moniliformis, Spirillum minus* and *Shigella dysenteriae*. Bacterial infections that can be treated using the active agents of the present invention can also be caused by bacteria such as gram-positive bacteria. Examples of gram-positive bacteria include, but are not limited to, bacteria of the genera *Listeria, Staphylococcus, Streptococcus, Bacillus, Corynebacterium, Peptostreptococcus*, and *Clostridium*. Furthermore, bacterial infections that can be treated using the active agents of the present invention can be caused by gram-positive bacteria including, but not limited to, *Listeria monocytogenes, Staphylococcus aureus, Streptococcus pyogenes, Streptococcus pneumoniae, Bacillus cereus, Bacillus anthraeis, Clostridium botulinum, Clostridium perfringens, Clostridium difficile, Clostridium tetani, Corynebacterium diphtheriae* and *Peptostreptococcus anaerobius*. In some embodiments, the gram-positive bacteria is methicillin-resistant *Staphylococcus aureus*.

Additional bacterial infections that can be treated using the active agents of the present invention can be caused by bacteria in the genera including, but not limited to, *Actinomyces*,

*Propionibacterium, Nocardia* and *Streptomyces*. Furthermore, bacterial infections that can be treated using the active agents of the present invention can be caused by bacteria including, but not limited to, *Actinomyces israeli, Actinomyces gerencseriae, Actinomyces viscosus, Actinomyces naeslundii, Propionibacterium propionicus, Nocardia asteroides, Nocardia brasiliensis, Nocardia otitidiscaviarum* and *Streptomyces somaliensis*.

Mycobacterial infections that can be treated by the compounds of the present invention can be caused by mycobacteria belonging to the mycobacteria families including, but not limited to, *Mycobacteriaceae*. Additionally, mycobacterial infections that can be treated by the compounds of the present invention can be caused by mycobacteria including, but not limited to, *Mycobacterium tuberculosis, Mycobacterium leprae, Mycobacterium avium-intracellulare, Mycobacterium kansasii*, and *Mycobacterium ulcerans*.

Spirochetal infections that can be treated using the active agents of the present invention can be caused by spirochetes belonging to the genera including, but not limited to, *Treponema, Leptospira*, and *Borrelia*. Additionally, spirochetal infections that can be treated using the active agents of the present invention can be caused by the spirochetes including, but not limited to, *Treponema palladium, Treponema pertenue, Treponema carateum, Leptospira interrogans, Borrelia burgdorferi*, and *Borrelia recurrentis*.

Rickettsial infections that can be treated using the active agents of the present invention can be caused by rickettsia belonging to the genera including, but not limited to, *Rickettsia, Ehrlichia, Orienta, Bartonella* and *Coxiella*. Furthermore, rickettsial infections that can be treated using the active agents of the present invention can be caused by rickettsia including, but not limited to, *Rickettsia rickettsii, Rickettsia akari, Rickettsia prowazekii, Rickettsia typhi, Rickettsia conorii, Rickettsia sibirica, Rickettsia australis, Rickettsia japonica, Ehrlichia chaffeensis, Orienta tsutsugamushi, Bartonella quintana*, and *Coxiella burni*.

Chlamydial infections that can be treated using the active agents of the present invention can be caused by chlamydia belonging to the genera including, but not limited to, *Chlamydia*. Furthermore, chlamydial infections that can be treated using the active agents of the present invention can be caused by chlamydia including, but not limited to, *Chlamydia trachomatis, Chlamydia caviae, Chlamydia pneumoniae, Chlamydia muridarum, Chlamydia psittaci*, and *Chlamydia pecorum*.

Mycoplasmal infections that can be treated using the active agents of the present invention can be caused by mycoplasma belonging to the genera including, but not limited to, *Mycoplasma* and *Ureaplasma*. In addition, mycoplasmal infections that can be treated using the active agents of the present invention can be caused by mycoplasma including, but not limited to, *Mycoplasma pneumoniae, Mycoplasma horninis, Mycoplasma genitalium*, and *Ureaplasma urealyticum*.

Fungal infections that can be treated using the active agents of the present invention can be caused by fungi belonging to the genera including, but not limited to, *Aspergillus, Candida, Cryptococcus, Coccidioides, Tinea, Sporothrix, Blastomyces, Histoplasma*, and *Pneumocystis*. Additionally, fungal infections that can be treated using the active agents of the present invention can be caused by fungi including, but not limited to, *Aspergillus fumigatus, Aspergillus flavus, Aspergillus niger, Aspergillus terreus, Aspergillus nidulans, Candida albicans, Coccidioides immitis, Cryptococcus neoformans, Tinea unguium, Tinea corporis, Tinea cruris, Sporothrix schenckii, Blastomyces dermatitidis, Histoplasma capsulatum*, and *Histoplasma duboisii*.

Viral infections that can be treated using the active agents of the present invention can be caused by viruses belonging to the viral families including, but not limited to, *Flaviviridae, Arenaviradae, Bunyaviridae, Filoviridae, Poxviridae, Togaviridae, Paramyxoviridae, Herpesviridae, Picornaviridae, Caliciviridae, Reoviridae, Rhabdoviridae, Papovaviridae, Parvoviridae, Adenoviridae, Hepadnaviridae, Coronaviridae, Retroviridae*, and *Orthornyxoviridae*. Furthermore, viral infections that can be treated using the active agents of the present invention can be caused by the viruses including, but not limited to, Yellow fever virus, St. Louis encephalitis virus, Dengue virus, Hepatitis G virus, Hepatitis C virus, Bovine diarrhea virus, West Nile virus, Japanese B encephalitis virus, Murray Valley encephalitis virus, Central European tick-borne encephalitis virus, Far eastern tick-born encephalitis virus, Kyasanur forest virus, Louping ill virus, Powassan virus, Omsk hemorrhagic fever virus, Kumilinge virus, Absetarov anzalova hypr virus, Ilheus virus, Rocio encephalitis virus, Langat virus, Lymphocytic choriomeningitis virus, Junin virus, Bolivian hemorrhagic fever virus, Lassa fever virus, California encephalitis virus, Hantaan virus, Nairobi sheep disease virus, Bunyamwera virus, Sandfly fever virus, Rift valley fever virus, Crimean-Congo hemorrhagic fever virus, Marburg virus, Ebola virus, Variola virus, Monkeypox virus, Vaccinia virus, Cowpox virus, Orf virus, Pseudocowpox virus, Molluscum contagiosum virus, Yaba monkey tumor virus, Tanapox virus, Raccoonpox virus, Camelpox virus, Mousepox virus, Tanterapox virus, Volepox virus, Buffalopox virus, Rabbitpox virus, Uasin gishu disease virus, Sealpox virus, Bovine papular stomatitis virus, Camel contagious ecthyma virus, Chamios contagious ecthyma virus, Red squirrel parapox virus, Juncopox virus, Pigeonpox virus, Psittacinepox virus, Quailpox virus, Sparrowpox virus, Starlingpox virus, Peacockpox virus, Penguinpox virus, Mynahpox virus, Sheeppox virus, Goatpox virus, Lumpy skin disease virus, Myxoma virus, Hare fibroma virus, Fibroma virus, Squirrel fibroma virus, Malignant rabbit fibroma virus, Swinepox virus, Yaba-like disease virus, Albatrosspox virus, Cotia virus, Embu virus, Marmosetpox virus, Marsupialpox virus, Mule deer poxvirus virus, Volepox virus, Skunkpox virus, Rubella virus, Eastern equine encephalitis virus, Western equine encephalitis virus, Venezuelan equine encephalitis virus, Sindbis virus, Semliki forest virus, Chilcungunya virus, O'nyong-nyong virus, Ross river virus, Parainfluenza virus, Mumps virus, Measles virus (rubeola virus), Respiratory syncytial virus, Herpes simplex virus type 1, Herpes simplex virus type 2, Varicella-zoster virus, Epstein-Barr virus, Cytomegalovirus, Human b-lymphotrophic virus, Human herpesvirus 7, Human herpesvirus 8, Poliovirus, Coxsackie A virus, Coxsackie B virus, ECHO-virus, Rhinovirus, Hepatitis A virus, Mengovirus, ME virus, Encephalomyocarditis (EMC) virus, MM virus, Columbia SK virus, Norwalk agent, Hepatitis E virus, Colorado tick fever virus, Rotavirus, Vesicular stomatitis virus, Rabies virus, Papilloma virus, BK virus, JC virus, B19 virus, Adeno-associated virus, Adenovirus, serotypes 3,7,14,21, Adenovirus, serotypes 11,21, Adenovirus, Hepatitis B virus, Coronavirus, Human T-cell lymphotrophic virus, Human immunodeficiency virus, Human foamy virus, Influenza viruses, types A, B, C, and Thogotovirus.

Plant viruses include viruses in the following groups: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picomaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites. Geminiviruses encompass viruses of the Genus *Mastrevirus*, Genus *Curtovirus*, and Genus *Begonzovirus*. Exemplary geminiviruses include, but are not limited to, Abutilon Mosaic Virus, Ageratum Yellow Vein Virus, Bhendi Yellow Vein Mosaic virus, Cassava African Mosaic Virus, Chino del Tomato Virus, Cotton Leaf Crumple Virus, Croton Yellow Vein Mosaic Virus, Dolichos Yellow Mosaic Virus, Horsegram Yellow Mosaic Virus, Jatropha Mosaic virus, Lima Bean Golden Mosaic Virus, Melon Leaf Curl Virus, Mung Bean Yellow Mosaic Virus, Okra Leaf Curl Virus, Pepper Hausteco Virus, Potato Yellow Mosaic Virus, Rhynchosia Mosaic Virus, Squash Leaf Curl Virus, Tobacco Leaf Curl Virus, Tomato Australian Leaf Curl Virus, Tobacco mosaic virus, Tomato Indian Leaf Curl Virus, Tomato Leaf Crumple Virus, Tomato Yellow Leaf Curl Virus, Tomato Yellow Mosaic Virus, Watermelon Chlorotic Stunt Virus, Watermelon Curly Mottle Virus, Bean Distortion Dwarf Virus, Cowpea Golden Mosaic Virus, Lupin Leaf Curl Virus, Solanum Apical Leaf Curling Virus, Soybean Crinkle Leaf Virus, Chloris Striate Mosaic Virus, Digitaria Striate Mosaic Virus, Digitaria Streak Virus, Miscanthus Streak Virus, Panicum Streak Virus, Pasalum Striate Mosaic Virus, Sugarcane Streak Virus, Tobacco Yellow Dwarf Virus, Cassava Indian Mosaic Virus, Serrano Golden Mosaic Virus, Tomato Golden Mosaic Virus, Cabbage Leaf Curl Virus, Bean Golden Mosaic Virus, Pepper Texas Virus, Tomato Mottle Virus, Euphorbia Mosaic Virus, African Cassava Mosaic Virus, Bean Calico Mosaic Virus, Wheat Dwarf Virus, Cotton Leaf Curl Virus, Maize Streak Virus, and any other virus designated as a Geminivirus by the International Committee on Taxonomy of Viruses (ICTV).

Badnaviruses are a genus of plant viruses having double-stranded DNA genomes. Specific badnavirus include cacao swollen shoot virus and rice tungro bacilliform virus (RTBV). Most badnavirus have a narrow host range and are transmitted by insect vectors. In the badnaviruses, a single open reading frame (ORF) may encode the movement protein, coat protein, protease and reverse transcriptase; proteolytic processing produces the final products. Exemplary. Badnaviruses include, but are not limited to Commelina Yellow Mottle Virus, Banana Streak Virus, Cacao Swollen Shoot Virus, Canna Yellow Mottle Virus, Dioscorea Bacilliform Virus, Kalanchoe Top-Spotting Virus, Piper Yellow Mottle Virus, Rice Tungro Bacilliform Virus, Schefflera Ringspot Virus, Sugarcane Bacilliform Virus, Aucuba Bacilliform Virus, Mimosa Baciliform Virus, Taro Bacilliform Virus, Yucca Bacilliform Virus, Rubus Yellow Net Virus, Sweet Potato Leaf Curl Virus, Yam Internal Brown Spot Virus, and any other virus designated as a Badnavirus by the International Committee on Taxonomy of Viruses (ICTV).

Caulimoviruses have double-stranded circular DNA genomes that replicate through a reverse transcriptase-mediated process, although the virus DNA is not integrated into the host genome. As used herein, Caulimoviruses include but are not limited to Cauliflower Mosaic Virus, Blueberry Red Ringspot Virus, Carnation Etched Ring Virus, Dahlia Mosaic Virus, Figwort Mosaic Virus, Horseradish Latent Virus, Mirabilis Mosaic Virus, Peanut Chlorotic Streak Virus, Soybean Chlorotic Mottle Virus, Strawberry Vein Banding Virus, Thistle Mottle Virus, Aquilegia Necrotic Mosaic Virus, Cestrum Virus, Petunia Vein Clearing Virus, Plantago Virus, Sonchus Mottle Virus, and any other virus designated as a Caulimovirus by the International Committee on Taxonomy of Viruses (ICTV).

The Nanoviruses have single-stranded circular DNA genomes. As used herein, Nanoviruses include but are not limited to Banana Bunchy Top Nanavirus, Coconut Foliar Decay Nanavirus, Faba Bean Necrotic Yellows Nanavirus, Milk Vetch Dwarf Nanavirus, and any other virus designated as a Nan.ovirus by the International Committee on Taxonomy of Viruses (ICTV).

Protozoans that can be treated using the active agents of the present invention include flagellates, amoebae, sporozoans and ciliates.

Parasitic infections that can be treated using the active agents of the present invention can be caused by parasites belonging to the genera including, but not limited to, *Entamoeba, Dientamoeba, Giardia, Balantidium, Trichomonas, Cryptosporidium, Isospora, Plasmodium, Leishmania, Trypanosoma, Babesia, Naegleria, Acanthamoeba, Balamuthia, Enterobius, Strongyloides, Ascaradia, Trichuris, Necator, Ancylostoma, Uncinaria, Onchocerca, Mesocestoides, Echinococcus, Taenia, Diphylobothrium, Hymenolepsis, Moniezia, Dicytocaulus, Dirofilaria, Wuchereria, Brugia, Toxocara, Rhabditida, Spirurida, Dicrocoelium, Clonorchis, Echinostoma, Fasciola, Fascioloides, Opisthorchis, Paragonimus*, and *Schistosoma*. Additionally, parasitic infections that can be treated using the active agents of the present invention can be caused by parasites including, but not limited to, *Entamoeba histolytica, Dientamoeba fragilis, Giardia lamblia, Balantidium coli, Trichomonas vaginalis, Cryptosporidium parvum, Isospora belli, Plasmodium malariae, Plasmodium ovale, Plasmodium falciparum, Plasmodium vivax, Leishmania braziliensis, Leishmania donovani, Leishmania tropica, Trypanosoma cruzi, Trypanosoma brucei, Babesia divergens, Babesia microti, Naegleria fowleri, Acanthamoeba culbertsoni, Acanthamoeba polyphaga, Acanthamoeba castellanii, Acanthamoeba astronyxis, Acanthamoeba hatchetti, Acanthamoeba rhysodes, Balamuthia mandrillaris, Enterobius vermicularis, Strongyloides stercoralis, Strongyloides fulleborni, Ascaris lumbricoides, Trichuris trichiura, Necator americanus, Ancylostoma duodenale, Ancylostoma ceylanicum, Ancylostoma braziliense, Ancylostoma caninum, Uncinaria stenoeephala, Onchocerca volvulus, Mesocestoides variabilis, Echinococcus granulosus, Iaenia solium, Diphylobothrium latum, Hymenolepis nana, Hymenolepis dirninuta, Moniezia expansa, Moniezia benedeni, Dicytocaulus viviparous, Dicytocaulus filarial, Dicytocaulus arnfieldi, Dirofilaria repens, Dirofilaria immitis, Wuchereria bancrofti, Brugia malayi, Toxocara canis, Toxocara cati, Dicrocoelium dendriticum, Clonorchis sinensis, Echinostoma, Echinostoma ilocanum, Echinostoma jassyenese, Echinostoma malayanum, Echinostoma caproni, Fasciola hepatica, Fasciola gigantica, Fascioloides magna, Opisthorchis viverrini, Opisthorchis felineus,*

*Opisthorchis sinensis, Paragonimus westermani, Schistosoma japonicum, Schistosoma mansoni, Schistosoma haematobium* and *Schistosoma haematobium.*

Additionally, some of the compounds described herein were found to possess anti-infective activity against certain bacteria, yeast and fungi. Accordingly, compounds described herein can be used for the treatment of topical bacterial, yeast and fungal infections. Such infections include *Staphylococcus aureus* and *Streptococcus* strains, e.g., pyogenes as well as the yeast strains *Candida albicans, Candida tropicalis* and *Saccharomyces cervisciae* and also include the following fungal strains: *Cryptococcus neoformans, Aspergillus fumigatus, Aspergillus flavus, Rhizopus arrihizus, Fusarium solani, Microsporidium canis, Microsporidium gypseum, Trichophyton equinium, Trichophyton mentagrophyt, Trichophyton rubrum* and *Epidermophyton floccsum.*

Allergic Conditions

As used herein "allergy" refers to any condition of the body mounting an attack on a specific foreign substance and can be further defined as a hypersensitivity or hyperimmunity caused by exposure to a particular antigen (allergen) resulting in an increase in reactivity to that antigen/allergen upon subsequent exposure. Allergic conditions can result from allergic reactions to foods, chemicals, plants, animals and a variety of air borne substances.

Exemplary allergens include pollens, feathers, moulds, animals, some foods, house dust, infections, such as common cold and influenza, emotional stress and excitement, vigorous exercise, cold air, occupational dusts and vapors, plastics, grains, metals, wood, air pollution, such as cigarette smoke, ozone, sulphur dioxide and auto exhaust, sleep (nocturnal asthma); household products, such as paint, cleaners and sprays, and drugs such as aspirin, heart medications, etc.

Allergic conditions include, but are not limited to, asthma, seasonal and perennial allergic rhinitis, sinusitis, conjunctivitis, drug allergy, food allergy and insect allergy, scombroid poisoning, psoriasis, urticaria, pruritus, eczema, rheumatoid arthritis, inflammatory bowel disease, chronic obstructive pulmonary disease, thrombotic disease, otitis media, atopic dermatitis, adolescent atopic deiniatitis, hives, contact dermatitis, senile dermatosis, pollenosis, ischemic diseases, cardia anaphylaxis and endotoxic shock.

Compounds of the present invention provide methods and pharmaceutical compositions for treating allergic conditions.

Inflammation

These compounds have been found to inhibit one or more of the enzymes 5-lipoxygenase, cyclooxygenase, and lyso-PAF: acetyl-CoA acetyltransferase. Additionally, pyridiniums derivative can inhibit the expression of adhesion molecules on human umbilical endothelial cell monolayers at low concentrations and are therefore indicative of being able to treat inflammations, infections and immune disorders.

Examples of inflammatory conditions, infectious conditions or immune disorders are those of the lungs, throat, mouth, joints, eyes, nose, bowel, and skin; particularly those associated with the infiltration of leucocytes into inflamed tissue. Conditions of the lung include asthma, adult respiratory distress syndrome, bronchitis and cystic fibrosis (which may additionally or alternatively involve the bowel or other tissues. Conditions of the thoat include laryngitis and oropharyngeal mucositis. Conditions of the mouth include gingivitis and periodontitis. Conditions of the joint include rheumatoid arthritis, rheumatoid spondylitis, osteoarthritis, gouty arthritis and other arthritic conditions. Inflammatory eye conditions include uveitis (including iritis) and conjunctivitis. Inflammatory nose conditions include rhinitis and chronic rhinosinusitis. Inflammatory bowel conditions include Crohn's disease, ulcerative colitis and distal proctitis. Skin diseases include those associated with cell proliferation, such as psoriasis, eczema and dermatitis (whether or not of allergic origin), and allergic-induced pruritis, such as prurigo. Other inflammatory conditions and immune disorders include tissue necrosis in chronic inflammation.

Research Assays

Stilbwium and thiazolium compounds exhibit staining properties and can bond to cloth, paper, wood plastic, glass, metal and other substrates, as well as skin and related living tissues, while retaining its red or pink or other associated coloration.

The pegylated compounds of the present invention can provide staining capabilities that may be visible in bright field and/or under fluorescence. Moreover, the compounds of the present invention provide a non-toxic staining option for viable cells and can provide repeatable staining of living cells. Additionally, the compounds of the present invention can be used in multiple assays of the same cultures. The compounds of the present invention can further provide detection of live cell mitotic division. Further, compounds of the present invention may exhibit stability at room temperature for a period of time sufficient to allow appropriate assays to be performed.

In particular, compounds of the present invention can be utilized as staining agents for DNA/RNA in their isolated state or for isolated cells and organelles. Also, the compounds may be utilized as nuclear staining agents for cell based assays. Further applications include using the compounds of the present invention to stain tissues and/or organs in whole animals as well as embryos, larvae, nematodes, insects and other parasites. In some embodiments, compounds of the present invention could be complexed with specific antibodies for imaging of specific organ tissues in the whole animal model systems. The term "antibody" or "antibody molecule" in the various grammatical forms as used herein refers to an immunoglobulin molecule (including IgG, IgE, IgA, IgM, IgD) and/or immunologically active portions of immunoglobulin molecules, i.e., molecules that contain an antibody combining site or paratope and can bind antigen.

Embodiments of the invention further include use of the compounds of the present invention in assays for determining the presence or absence of a cell, an analyte, a nucleic acid or a microorganism in a sample suspected of containing a cell, an analyte, a nucleic acid or a microorganism, the assay including combining the sample with a labeling reagent to form a labeled cell, nucleic acid or microorganism, the labeling reagent including a dye which directly stains the cell, analyte, nucleic acid or microorganism to provide a stained sample comprising a stained cell, analyte, nucleic acid or microorganism, wherein the dye is a compound described herein.

Accordingly, in some embodiments, the invention features a technique for determining the presence, location, or quantity of a cell, and thus, cellular organelles such as the nucleus, smooth and/or rough endoplasmic reticulum, centrosome, cytoskeleton, cell wall, cell membrane, flagella, cilia, chloroplast, mitochondria, golgi apparatus, ribosome, lysosome, centriole, acrosome, glyoxysome, secretory vesicle, peroxisome, vacuole, melanosome, myofibril and parenthesome. In other embodiments, the invention features a technique for determining the presence, location, quantity and/or health of cells, analytes and microorganisms.

Embodiments of the present invention further include a probe including a ligand or antibody and a compound described herein. The probe can be used to detect cells, analytes, nucleic acids and microorganisms.

"Cell" as used herein refers to a basic component of a living or fixed organism and includes organelles. Thus, detecting the presence of a cell, assaying a cell, staining a cell, etc. can refer to a whole cell or at least one organelle of the cell. According to embodiments of the present invention, cells may be plant or animal cells. As recognized by one skilled in the art, "organelles" as used herein refer to cellular components or structures suspended in the cytoplasm including those providing a boundary therefor and having specialized functions. Organelles include, but are not limited to, the nucleus, smooth and/or rough endoplasmic reticulum, centrosome, cytoskeleton, cell wall, cell membrane, flagella, cilia, chloroplast, mitochondria, golgi apparatus, ribosome, lysosome, centriole, acrosome, glyoxysome, secretory vesicle, peroxisome, vacuole, melanosome, myofibril and parenthesome.

"Dye" as used herein refers to a substance that imparts color and/or fluorescence and/or is quantifiable or distinguishable. The color and/or fluorescence can be temporary, semi-permanent or permanent.

"Analyte" as used herein refers to the substance or chemical constituent that undergoes analysis. For example, an analyte can be a molecule, protein, chemical substance, etc. that can be detected as a result of biological, chemical or clinical testing to evaluate the same. Analytes can include, but are not limited to, ions, metabolites such as glucose and urea, trace metabolites such as hormones, drugs and steroid hormones, gases such as respiratory gases, anesthetic gases, toxic gases and flammable gases, toxic vapors, proteins and nucleic acids, antigens, and antibodies and microorganisms.

Embodiments of the present invention further include kits for staining cells, analytes, nucleic acids and/or microorganisms.

Agricultural Uses

The compounds according to the present invention are also particularly effective against powdery mildews and rusts, pyrenophora, rhynchosporium, tapesia, fusarium and leptosphaeria fungi, in particular against pathogens of monocotyledonous plants such as cereals, including wheat and barley. They are furthermore particularly effective against downy mildew species, powdery mildews, leaf spot diseases and rusts in dicotyledonous plants.

The amount of the compounds of the invention to be applied, will depend on various factors such as the compound employed, the subject of the treatment (substrate, plant, soil, seed), the type of treatment (e.g., spraying, dusting, seed dressing), the purpose of the treatment (prophylactic or therapeutic), the type of fungi and/or bacteria to be treated and the application time.

The fungicidal and/or bactericidal combinations are of particular interest for controlling a large number of fungi and/or bacteria in various crops or their seeds, especially wheat, rye, barley, oats, rice, maize, lawns, cotton, soybeans, coffee, sugarcane, fruit and ornamentals in horticulture and viticulture, in vegetables such as cucumbers, beans and cucurbits, and in field crops such as potatoes, peanuts, tobacco and sugarbeets.

The term "controlling" means reducing, inhibiting, lessening, restraining, hampering, etc.

The combinations are applied by treating the fungi and/or bacteria or the seeds, plants or materials threatened by fungus attack, or the soil with a fungicidally and/or bacterially effective amount of the active ingredients.

The agents may be applied before or after infection of the materials, plants or seeds by the fungi and/or bacteria.

When applied to the plants, the compounds described herein are applied at a rate of 25 to 250 g/ha, generally from 50 to 150 g/ha, e.g., 75, 100, 125 or 150 g/ha, in association with 20 to 2000 g/ha, generally from 20 to 1000 g/ha.

In agricultural practice, the application rates of the combination depend on the type of effect desired, and range from 0.02 to 3 kg of active ingredient per hectare.

When the active ingredients are used for treating seed, rates of 0.001 to 50 g a.i. per kg, and generally from 0.01 to 10 g per kg of seed are generally sufficient.

The composition of the invention can be employed in any conventional form, for example in the form of a twin pack, an instant granulate, a flowable formulation, an emulsion concentrate or a wettable powder or surfactant (such as sodium lauryl sulfate and sodium lauryl sulfate salts), in combination with agriculturally acceptable adjuvants. Such compositions may be produced in conventional manner, e.g., by mixing the active ingredients with appropriate adjuvants (diluents or solvents and optionally other formulating ingredients such as surfactants). Also conventional slow release formulations may be employed where long lasting efficacy is intended.

Particular formulations to be applied in spraying forms such as water dispersible concentrates or wettable powders may contain surfactants such as wetting and dispersing agents, e.g., the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g., as slow release capsules or microcapsules.

In general, the formulations include from 0.01 to 90% by weight of active agent, from 0 to 20% agriculturally acceptable surfactant and 10 to 99.99% solid or liquid adjuvant(s), the active agent consisting of at least the compound of formula I, and optionally other active agents, particularly microbides or conservatives or the like. Concentrated forms of compositions generally contain in between 2 and 80%, generally from between 5 and 70% by weight of active agent. Application forms of the formulation may for example contain from 0.01 to 20% by weight, generally from 0.01 to 5% by weight of active agent. Whereas commercial products will generally be formulated as concentrates, the end user will normally employ dilute formulations.

Additionally, the color of the present compounds may be removed by a type of "bleaching." It is well recognized in the art (cf. for instance B. C. Saunders et al., Peroxidase, London, 1964, p. 10 ff.) that peroxidases act on various amino and phenolic compounds resulting in the production of a color. In view of this, it must be considered surprising that peroxidases (and certain oxidases) may also exert an effect on colored substances in solution such that dye transfer is inhibited. While the mechanism governing the ability of these enzymes to effect dye transfer inhibition has not yet been elucidated, it is currently believed that the enzymes act by reducing hydrogen peroxide or molecular oxygen and oxidizing the colored substance (donor substrate) dissolved or dispersed in the wash liquor, thereby either generating a colorless substance or providing a substance which is not adsorbed to the fabric or building material.

Additionally, a liquid composition of matter according to the present invention may be formed and may be mixed with and/or diluted by an excipient. When the excipient serves as a diluent, it may be a solid, semi-solid, or liquid material which acts as a vehicle, carrier, or medium for the composition of matter. Various suitable excipients will be understood by those skilled in the art and may be found in the *National Formulary,* 19: 2404-2406 (2000), the disclosure of pages 2404 to 2406 being incorporated by reference herein in their entirety. Preferable excipients include butanedioal and EDTA. Examples of suitable excipients include, but are not limited to, starches, gum arabic, calcium silicate, microcrystalline cellulose, methacrylates, shellac, polyvinylpyrrolidone, cellulose, water, syrup, and methylcellulose. An aqueous medium may include an active ingredient or ingredients, a quantity of one or more surfactants sufficient to dissolve or suspend said active ingredients uniformly throughout the medium and other manufacturing additives as known to the art. The latter include granulating-binding agents such as gelatin; natural gums, such as acacia, tragacanth; starches, sodium alginate, sugars, polyvinylpyrrolidone; cellulose derivatives such as hydroxypropylrnethylcellulose, polyvinyloxoazolidones; pharmaceutical fillers such as lactose, microcrystalline cellulose, dicalcium phosphate, tricalcium phosphate, calcium sulfate, dextrose, mannitol, sucrose; tabletting lubricants if needed such as calcium and magnesium stearate, stearic acid, talc, sterotex (alkaline stearate). The term "aqueous medium" for one ingredient of one of the embodiments of the invention is used within the custom of the art. Primarily, it connotes a water medium, with added water-miscible solvents such as isopropanol or ethanol when needed, to support the active ingredient.

Industrial Use

The compounds of the present invention can be used to treat all areas and substrates where algae, molds, mildew, fungi and bacteria can grow. Examples include, but are not limited to, wood, air ducts, lumber, decks, buoys, seawalls, retaining walls, docks, pilings, watercrafts, boats, pipes, stucco, tiles, paint, insulation, roofs, roofing materials, building materials, metal, concrete and cement based materials, plasters, asphalts, ceramics, stucco, grout, plastics, glass, computer parts, semiconductor devices and parts used in semiconductor fabrication, food packaging, recreational water bodies, such as swimming pools, pool surfaces, hot tubs, and spas, wall coverings, siding materials, flooring, filtration systems, cooling towers, substrates, in general, other substrates as desired, etc. The compound can be applied to the surface of the substrate or incorporated into the substrate during the fabrication process of the substrate or subsequent thereto.

Embodiments of the present invention further include application of the formulations of the present invention onto various articles of manufacture, substrates and/or materials and/or use in processes listed above as well as incorporation into the products to form an integral part of the material. For example, formulations of the present invention may be coated or sprayed onto and/or incorporated into the substrate forming the medical device, such as a stent, for the prevention of biofilm formation. Formulations of the present invention may be coated onto a cement-based material and/or included in the cement mix during formation of the cement-based material. Lumber may be pressure-treated with the formulations described herein and/or soaked with a solution including the formulations. Fabrics may be coated or sprayed or soaked with the formulations described herein, or individual strands may be treated prior to the weaving or fabrication process. Other building materials such as wall board, masonite, particle board, etc. may be treated with formulations described herein, or the formulations may be added to the slurry or mixture during the fabrication of the materials so that the compounds of the present invention become an integral part of intermediate and final materials. The amount of the compound to be added during the fabrication process can be determined through routine experimentation and in view of government regulations through agencies such as the Environmental Protection Agency (EPA), U.S. Food and Drug Administration (FDA) and U.S. Department of Agriculture (USDA), as well as foreign counterparts.

Another embodiment of the present invention can include the stilbazium and thiazolium compounds being encapsulated. As used herein the term "microcapsules" is intended to contemplate single molecules, encapsulated discrete particulate, multiparticulate, liquid multicore and homogeneously dissolved active components. The encapsulation method may provide either a water soluble or oil soluble active component encapsulated in a shell matrix of either a water or oil soluble material. The microencapsulated active component may be protected from oxidation and hydration, and may be released by melting, rupturing, biodegrading, or dissolving the surrounded shell matrix or by slow diffusion of the active component through the matrix. Microcapsules usually fall in the size range of between 1 and 2000 microns, although smaller and larger sizes are known in the art.

The compounds of the present invention may be placed in a capsule or microcapsule or hollow fiber type used for distribution. They may also be dispersed in a polymeric material or held as a liquid.

An additional active ingredient can be placed with a compound of the present invention in an encapsulation. Examples of the active ingredient having repellent activity may include triethylene glycol monohexyl ether and N,N-diethyl-m-triamide. See U.S. Pat. No. 6,419,943. Examples of the active ingredient having aromatic activity include geraniol, limonene, benzyl alcohol, esters of a $C_{6-20}$ hydrocarbon, ethers, aldehydes and alcoholic compounds. Examples of the active ingredient having pesticidal activity include insecticides such as salithion, diazinon and chlorpyrifos and bactericides such as thiophanate-methyl and captan.

Such constituents can be encapsulated, as is desired in the case of phase change materials. Such encapsulated constituents can further be encapsulated in microcapsules. The microcapsules can be made from a wide variety of materials, including polyethylene, polypropylenes, polyesters, polyvinyl chloride, tristarch acetates, polyethylene oxides, polypropylene oxides, polyvinylidene chloride or fluoride, polyvinyl alcohols, polyvinyl acetates, urethanes, polycarbonates, and polylactones. Further details on microencapusulation are to be found in U.S. Pat. Nos. 5,589,194 and 5,433,953. Microcapsules suitable for use in the base materials of the present invention have diameters from about 1.0 to 2,000 microns.

No particular limitation is imposed on the shape for holding the active ingredient. In other words, there are various forms for holding the active ingredient by a holding mixture. Specific examples include microcapsules in which the surface of the active ingredient has been covered with the holding mixture; and products processed into a desired shape, each being obtained by kneading the active ingredient in the holding mixture or forming a uniform solution of the holding mixture and the active ingredient, dispersing the active ingredient in the holding mixture by the removal of the solvent or the like and then processing the dispersion into a desired shape such as single molecule, liquid, sphere, sheet, film, rod, pipe, thread, tape or chip. In addition, these processed products having a surface covered with a barrier layer for controlling the release of the active ingredient and those coated with an adhesive for improving applicability can be given as examples. As further examples, those obtained by filling the active ingredient in the holding mixture processed into a form of a capillary tube, heat sealing both ends of the capillary tube and then encapsulating the active ingredient therein; and those obtained by centrally cutting the above-mentioned capillary tube into two pieces, thereby having each one end as an opening.

The container formed of a holding mixture which container has an active ingredient enclosed therein as a liquid phase to secure uniform release ability over a long period of time. As such shape, tube-, bottle- or bag-shaped container is used generally.

When the mixture is formed into a container, the sustained release layer desirably has a thickness of at least 0.002 mm for effecting stable sustained release. There occurs no particular problem when the sustained release layer has a thickness not smaller than 0.002 mm, but that ranging from 0.005 mm to 5 mm can be used. When it exceeds 5 mm, the release amount of the compound tends to become too small.

For solids, the release surface area of the sustained release preparation formed of such a container is desirably 0.001 cm$^2$ or larger. A range of from 0.01 cm$^2$ to 1 cm$^2$ may be used.

When the active ingredient is enclosed and held in a container of the sustained release preparation, said container having been formed of a holding mixture, it may be enclosed in portions. The enclosed amount can be 0.5 mg to 5 mg, and may be 1 mg, 2 mg, 3 mg, or 4 mg.

As the shape of the container formed of a holding mixture, a tube, bottle and bag can be used. In the case of the tube-shaped preparation, that having an internal diameter of 0.4 mm to 10 mm can be used. Internal diameters smaller than 0.4 mm make it difficult to fill the active ingredient in the container, while those larger than 10 mm make it difficult to conduct encapsulation. The bottle-shaped preparation is formed by blow molding or injection molding and generally has an internal volume of 0.1 to 200 ml. The bottle having an internal volume less than 0.1 ml cannot be formed easily, while that having an internal volume greater than 200 ml is not economical because there is a large difference between the amount of the active ingredient filled therein and the internal volume: In the case of a bag-shaped preparation, the amount of the active ingredient filled in the bag is desirably 1 mg to 100 g.

The biodegradable sustained-release preparation according to the first group of the present invention should retain its essential performance during application so that a pigment or dye, or various stabilizers such as ultraviolet absorber/blocker or antioxidant may be added to the holding mixture in order to improve the weather resistance. Alternatively, it is possible to add such an additive to the active ingredient enclosed in the container formed of a holding mixture.

As used herein, the term "controlled release" is intended to mean the release of a bio-active at a pre-selected or desired rate. This rate will vary depending upon the application. Desirable rates include fast or immediate release profiles as well as delayed, sustained or sequential release profiles. Combinations of release patterns, such as initial spiked release followed by lower levels of sustained release of the bio-active are also contemplated by the present invention.

As used herein, the term "bio-active" includes therapeutic agents such as pharmaceutical or pharmacological active agents, e.g., drugs and medicaments, as well as prophylactic agents, diagnostic agents and other chemicals or materials useful in treating or preventing conditions, infections and/or diseases. The compositions of the present invention are particularly effective in plants and other organisms.

In accordance with the present invention there is provided a microcapsule bacteriocide and/or fungicide composition comprising microcapsules each having a polyurea shell including as an integral part of said shell a photostable ultraviolet light absorbent compound or blocker compound having a log molar extinction coefficient of from 2 to 5 with respect to radiation having wave lengths in the range of from 270 to 350 nanometers and a liquid fill capable of slowly permeating the shell and comprising a pyridinium salt and a biological synergist therefor.

As used herein "photosensitive material" refers to all compositions and materials designed to block and/or absorb ultraviolet light. This term also refers to all photoprotective and photoresistant agents.

As herein used "surfactant" refers to all compositions including surfactant salt compositions that are capable of forming emulsions, micro-emulsions, suspensions, etc.

The entire microcapsule composition can include of 60-90 percent of liquid fill and 40-10 percent of shell wall, the liquid fill comprising 5-40 percent of pyridinium salt, 25-50 percent of biological synergist and 20-40 percent of a water-immiscible organic solvent and the shell including as an integral part thereof 0.5-20 percent of photostable ultraviolet light absorbent compound (all percentages being based on the weight of the entire microcapsule composition).

The pyridinium salts (also known as pyridinium compounds) remain inside the microcapsules while the composition is packaged and in storage, i.e., in a closed container due to the partial pressure of the pyridinium salt surrounding the microcapsules. When the product is applied as a bacteriocide and/or fungicide, the pyridinium salt, releases slowly (the actual speed of release depending upon the thickness and porosity of the capsule walls). The pyridinium salt is chemically stable during storage and after application until it permeates the capsule walls. At that time it becomes available as a bacteriocide and/or fungicide until degraded. Since the fill permeates the shell wall slowly, the microcapsule product has a long effective bacteriocide and/or fungicide life and may be stored for extended periods (e.g., for 6 months and more). The process is also applicable to the thiazolium salts (thiazolium compounds) described herein.

Suitable fill stabilizers absorb ultraviolet radiation in the range of 270-350 nanometers and convert it to a harmless form. They have a high absorption coefficient in the near ultraviolet portion of the spectrum (e.g., a log molar extinction coefficient of from about 2 to 5) but only minimal absorption in the visible portion of the spectrum. They do not exhibit any substantial chemical reaction with the isocyanate groups and primary amine groups of the shell forming compounds during the microencapsulation process. Among the compounds which can be used as fill stabilizers are substituted benzophenones such as 2,4-dihydroxy benzophenone, 2-hydroxy-4-methoxy benzophenone, 2-hydroxy-4-octyloxy benzophenone, etc.; the benzotriazoles such as 2-(2-hydroxy-5'-methylphenyl)benzotriazole, 2-(3',5'-diallyl-2'-hydroxylphenyl)benzotriazole, etc.; substituted acrylates such as ethyl 2-cyano-3,3-diphenyl acrylate, 2-ethylhexyl-2-cyano-3,3-diphenyl acetate, etc.; salicylates such as phenyl salicylates, 5-butyl phenyl salicylate, etc.; and nickel organic compounds such as nickel bis(octylphenol)sulfide, etc. Additional examples of each of these classes of fill stabilizers may be found in Kirk-Othmer, Encyclopedia of Chemical Technology. The fill stabilizers may comprise up to 5 percent, and are generally from 0.01 to 2 percent, by weight of the microcapsule composition.

The embodiments of the invention also provide a process for controlling fungal and bacterial activity by contacting the fungi and bacteria with an effective level of the compositions including stilbazium and/or thiazolium compounds as recited throughout. Contact may be accomplished directly, for example, by atomization of the composition into the air in the faun of a spray. Alternatively, compositions of the present invention may be provided in various other forms, for example in sheet materials carrying the microcapsules, (e.g., tapes coated or impregnated with the microcapsules) that may be placed in areas where the fungi and bacteria may grow.

Another embodiment of the present invention may include heat sensitive materials which are excellent in preservation stability especially in resistance to light, and microcapsules having an ultraviolet absorber enclosed therein, which are applicable to various fields. Desirable constituents which may be present in a base material include materials which can absorb heat and protect an underlying material from overheating. Thermal energy is absorbed by the phase change of such materials without causing an increase in the temperature of these materials. Suitable phase change materials include paraffinic hydrocarbons, that is, straight chain hydrocarbons represented by the formula $C_nH_{n+2}$, where n can range from 13 to 28. Other compounds which are suitable for phase change materials are 2,2-dimethyl-1,3-propane diol (DMP), 2-hydroxymethyl-2-methyl-1,3-propane diol (HMP) and similar compounds. Also useful are the fatty esters such as methyl palmitate. Phase change materials that can be used include paraffinic hydrocarbons.

Heat sensitive recording materials are well known which utilize a color forming reaction between a colorless or light-colored basic dye and an organic or inorganic color acceptor to obtain record images by thermally bringing the two chromogenic substances into contact with each other. Such heat sensitive recording materials are relatively inexpensive, are adapted for use with recording devices which are compact and easy to maintain, and have therefore found wide applications as recording media for facsimile systems, various computers, etc. In order to improve light resistance of heat sensitive recording materials a finely divided ultraviolet absorber or blocker can be added to the heat sensitive recording layer or protective layer.

Another embodiment of the present invention is to provide microcapsules which have excellent retainability of ultraviolet absorber, difficult to be ruptured at a usual pressure and are excellent in ultraviolet ray absorbing efficiency.

Embodiments of the present invention can include a heat sensitive recording material comprising a substrate, a recording layer fondled over the substrate and containing a colorless or light-colored basic dye and a color acceptor, and a protective layer fanned over the recording layer, the recording material being characterized in that microcapsules having an ultraviolet absorber enclosed therein and having substantially no color forming ability are incorporated in the protective layer.

Further, the present invention provides microcapsules having an ultraviolet absorber and as required an organic solvent enclosed therein, which have capsule wall film of synthetic resin and mean particle size of 0.1 to 3 μm.

The following are examples of ultraviolet absorbers that may be used in the present invention as additional ingredients:

Phenyl salicylate, p-text-butylphenyl salicylate, p-octylphenyl salicylate and like salicylic acid type ultraviolet absorbers; 2,4-dihydroxybenzophenone, 2-hydroxy-4-methoxybenzophenone, 2-hydroxy-4-octyloxybenzophenone, 2-hydroxy-4-dodecyloxybenzophenone, 2,2'-dihydroxy-4-methoxybenzophenone, 2,2,'-dihydroxy-4,4'-dimethoxybenzophenone, 2-hydroxy-4-methoxy-5-sulfobenzophenone and like benzophenone type ultraviolet absorbers; 2-ethylhexyl 2-cyano-3,3-diphenyt-acrylate, ethyl 2-cyano-3,3-diphenylacrylate and like cyanoacrylate type ultraviolet absorbers; bis(2,2,6,6-tetramethyl-4-piperidyl)sebacate, bis(2,2,6,6-tetramethyl-4-piperidyl)succinate, bis(1,2,2,6,6-pentamethyl-4-piperidyl) 2-(3,5-di-tert-butyl-4-hydroxybenzyl)-2-n-butyl malonate and like hindered amine type ultraviolet absorbers; 2-(2'-hydroxyphenyl)benzotriazole, 2-(2'-hydroxy-5'-methylphenyl)benzotriazole, 2-(2'-hydroxy-5-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-butylphenyl)-5-tert-butylbenzotriazole, 2-(2'-hydroxy-3',5'-di-tert-amylphenyl)benzotriazole, 2-(2'-hydroxy-3',5'-di-tert-amylphenyl)-5-tert-amylbenzotriazole, 2-(2'-hydroxy-3',5'-di-tert-amylphenyl)-5-methoxybenzotriazole, 2-[2'-hydroxy-3'-(3",4",5",6"-tetrahydrophthalimido-methyl)-5'-methylphenyl]benzotriazole, 2-(2'-hydroxy-5'-tert-octylphenyl)benzotriazole, 2-(2'-hydroxy-3'-sec-butyl-5'-tert-butylphenyl)benzotriazole, 2-(2'-hydroxy-3'-tert-amyl-5'-phenoxyphenyl)-5-methylbenzotriazole, 2-(2'-hydroxy-5'-n-dodecylphenyl)benzotriazole, 2-(2'-hydroxy-5'-sec-octylophenyl)-5-phenylbenzotriazole, 2-(2'-hydroxy-3'-tert-amyl-5'-phenylphenyl)-5-methoxybenzotriazole, 2-[2'-hydroxy-3',5'-bis(α,α-dimethylbenzyl)phenyl]benzotriazole and like benzotriazole type ultraviolet absorbers which are solid at ordinary temperature; 2-(2'-Hydroxy-3'-dodecyl-5'-methylphenyl)-benzotriazole, 2-(2'-hydroxy-3'-undecyl-5'-methylphenyl)-benzotriazole, 2-(2'-hydroxy-3'-tridecyl-5'-methylphenyl)-benzotriazole, 2-(2'-hydroxy-3'-tetradecyl-5'-methylphenyl)-benzotriazole, 2-(2'-hydroxy-3'-pentadecyl-5'-methylphenyl)-benzotriazole, 2-(2'-hydroxy-3'-hexadecyl-5'-methylphenyl)-benzotriazole, 2-[2'-hydroxy-4'-(2"-ethylhexyl)oxyphenyl]-benzotriazole, 2-[2'-hydroxy-4'-(2"-ethylheptyl)oxyphenyl]-benzotriazole, 2-[2'-hydroxy-4'-(2"-ethyloctyl)oxyphenyl]-benzotriazole, 2-[2'-hydroxy-4'-(2"-propyloctyl)oxyphenyl]-benzotriazole, 2-[2'-hydroxy-4'-(2"-propylheptyl)oxyphenyl]-benzotriazole, 2-[2'-hydroxy-4'-(2"-propylhexyl)oxyphenyl]-benzotriazole, 2-[2'-hydroxy-4'-(1"-ethylhexyl)oxyphenyl]-benzotriazole, 2-[2'-hydroxy-4'-(1"-ethylheptyl)oxyphenyl]-benzotriazole, 2-[2'-hydroxy-4'-(1"-ethyloctyl)oxyphenyl]-benzotriazole, 2-[2'-hydroxy-4'-(1"-propyloctyl)oxyphenyl]-benzotriazole, 2-[2'-hydroxy-4'-(1"-propylheptyl)oxyphenyl]-benzotriazole, 2-[2'-hydroxy4'-(1"-propylhexyl)oxyphenyl]-benzotriazole, 2-(2'-hydroxy-3'-sec-butyl-5'-tert-butylphenyl-5-n-butyl-benzotriazole, 2-(2'-hydroxy-3'-sec-butyl-5'-tert-butylphenyl)-5-tert-pentyl-benzotriazole, 2-(2'-hydroxy-3'-sec-butyl-5'-tert-butylphenyl)-5-n-pentyl-benzotriazole, 2-(2'-hydroxy-3'-sec-butyl-5'-tert-pentylphenyl)-5-tert-butylbenzotriazole, 2-(2'-hydroxy-3'-sec-butyl-5'-tert-pentylphenyl)-5-n-butylbenzoazole, 2-(2'-hydroxy-3',5'-di-tert-butylphenyl)-5-sec-butylbenzotriazole, 2-(2'-hydroxy-3',5'-di-tert-pentylphenyl)-5-sec-butylbenzotriazole, 2-(2'-hydroxy-3'-tert-butyl-5'-tert-pentylphenyl)-5-sec-butylbenzotriazole, 2-(2'-hydroxy-3',5'-di-sec-butylphenyl)-5-chlorobenzotriazole, 2-(2'-hydroxy-3',5'-di-sec-butylphenyl)-5-methoxybenzotriazole, 2-(2'-hydroxy-3',5'-di-sec-butylphenyl)-5-tert-butylbenzotriazole, 2-(2'-hydroxy-3',5'-di-sec-butylphenyl)-5-n-butylbenzotriazole, octyl 5-tert-butyl-3-(5-chloro-2H-benzotriazole-2-yl)-4-hydroxybenzene-propionate, condensate of methyl 3-[3-tert-butyl-5-(2H-benzotriazole-2-yl)-4-hydroxyphenyl]propionate and polyethylene glycol (molecular weight: about 300) and like benzotriazole type ultraviolet absorbers which are liquid at ordinary temperature. Of course, the ultraviolet absorber is not limited to thereabove and can be used as required in a mixture of at least two of them.

Although the amount of ultraviolet absorber to be used is not limited specifically, the amount can be adjusted to 10 to 500 parts by weight, and generally from 20 to 250 parts by weight of the ultraviolet absorber versus the active ingredient.

The microcapsules for use in the present invention can be prepared by various known methods. They are prepared generally by emulsifying and dispersing the core material (oily liquid) comprising an ultraviolet absorber and, if necessary, an organic solvent in an aqueous medium, and forming a wall film of high-molecular-weight substance around the resulting oily droplets.

Examples of useful high-molecular-weight substances for forming the wall film of microcapsules are polyurethane resin, polyurea resin, polyamide resin, polyester resin, polycarbonate resin, aminoaldehyde resin, melamine resin, polystyrene resin, styrene-acrylate copolymer resin, styrene-methacrylate copolymer resin, gelatin, polyvinyl alcohol, etc. Especially, microcapsules having a wall film of a synthetic resin, particularly polyurea resin, polyurethane resin and aminoaldehyde resin among other resins have excellent retainability of an ultraviolet absorber and high heat resistance and accordingly exhibit the outstanding additional effect to serve the function of a pigment which is to be incorporated in the protective layer for preventing sticking to the thermal head. Moreover, microcapsules having a wall film of polyurea resin or polyurethane resin are lower in refractive index than microcapsules with wall films of other materials and usual pigments, are spherical in shape and are therefore usable favorably because even if present in a large quantity in the protective layer, they are unlikely to reduce the density of record images (so-called whitening) owing to irregular reflection of light. Further, polyurea resin and polyurethane resin are more elastic than aminoaldehyde resin and therefore polyurea resin and polyurethane resin are generally used as a wall film for microcapsules which are used under a condition of high pressure. On the other hand, microcapsules having a wall film made from aminoaldehyde resin have a merit that the wall film can be controlled in thickness without depending on particle size of emulsion because the microcapsules can be prepared by adding a wall-forming material after emulsification of a core material.

The present invention may also include organic solvent together with an ultraviolet absorber. The organic solvent is not particularly limited and various hydrophobic solvents can be used which are used in a field of pressure sensitive manifold papers. Examples of organic solvents are tricresyl phosphate, octyldiphenyl phosphate and like phosphates, dibutyl phthalate, dioctyl phthalate and like phthalates, butyl oleate and like carboxylates, various fatty acid amides, diethylene glycol dibenzoate, monoisopropylnaphthalene, diisopropylnaphthalene and like alkylated naphthalenes, 1-methyl-1-phenyl-1-tolylmethane, 1-methyl-1-phenyl-1-xylylmethane, 1-phenyl-1-tolylmethane and like alkylated benzenes, isopropylbiphenyl and like alkylated biphenyls, trimethylolpropane triacrylate and like acrylates, ester of polyol and unsaturated carboxylic acid, chlorinated paraffin and kerosene. These solvents can be used individually or in a mixture of at least two of them. Among these hydrophobic media having a high boiling point, tricresyl phosphate and 1-phenyl-1-tolylmethane are desirable since they exhibit high solubility in connection with the ultraviolet absorber to be used in the present invention. Generally, the lower the viscosity of the core material, the smaller is the particle size resulting from emulsification and the narrower is the particle size distribution, so that a solvent having a low boiling point is conjointly usable to lower the viscosity of the core material. Examples of such solvents having a low boiling point are ethyl acetate, butyl acetate, methylene chloride, etc.

The amount of organic solvent to be used should be suitably adjusted according to the kind and amount of ultraviolet absorber to be used and the kind of organic solvent and is not limited specifically. For example in case of using an ultraviolet absorber which is liquid at ordinary temperature, an organic solvent is not necessarily used. However, in case of using an ultraviolet absorber which is solid at ordinary temperature, since it is desired that the ultraviolet absorber be in a fully dissolved state in the microcapsules, the amount of organic solvent, for example in case of microcapsules of polyurea resin or polyurethane resin, is adjusted generally from to usually 10 to 60 wt. %, or from 20 to 60 wt: %, based on the combined amount of organic solvent, ultraviolet absorber and wall-forming material. Further, in case of microcapsules of aminoaldehyde resin, the amount of organic solvent is adjusted to usually 50 to 2000% by, weight, generally from 100 to 1000% by weight of ultraviolet absorber.

While the amount of capsule wall-forming material to be used is not limited specifically either, preservation for a long period of time is likely to permit the organic solvent in the microcapsules to be released to decrease contemplated effects or give adverse effects to a heat sensitive recording material and other materials having microcapsules used, so that it is desired to use a larger amount of wall-forming material than is the case with usual microcapsules used in a pressure sensitive recording material, etc. Thus, for example in case of using microcapsules of polyurea resin or polyurethane resin, the wall-forming material is used preferably in an amount of 20 to 70 wt. %, more preferably 25 to 60 wt. %, based on the combined amount of the three components, i.e., the organic solvent which is used as required, ultraviolet absorber and wall-forming material. In case of using microcapsules of aminoaldehyde resin, the wall-forming material is used usually in an amount of 30 to 300% by weight, preferably 35 to 200% by weight of the core material containing as main components ultraviolet absorber and as required organic solvent.

Additionally, an absorber may be utilized. An absorber should be selected which reduces the sensitivity of the microcapsule in those portions of its spectral sensitivity range which interfere with the exposure of microcapsules at other wavelengths (its inactive range) without overly reducing the sensitivity of the Microcapsule in those portions of the spectral sensitivity range in which the microcapsule is intended to be exposed (its active range). In some cases it may be necessary to balance the absorption characteristics of the absorber in the active range and the inactive range to achieve optimum exposure characteristics. Generally absorbers having an extinction coefficient greater than about 100/M cm in the inactive range and less than about 100,000/M cm in the active range of the microcapsule are used. When the absorber is directly incorporated into the photosensitive composition, ideally, it should not inhibit free radical polymerization, and it should not generate free radicals upon exposure.

The absorbers used in the present invention can be selected from among those absorbers which are known in the photographic art. Examples of such compounds include dyes conventionally used as silver halide sensitizing dyes in color photography (e.g., cyanine, merocyanine, hemicyartine and styryl dyes) and ultraviolet absorbers. A number of colored dyes which absorb outside the desired sensitivity range of the microcapsules and do not absorb heavily within the range could also be used as absorbers in the present invention. Among these, Sudan I, Sudan II, Sudan III, Sudan Orange G, Oil Red O, Oil Blue N, and Fast Garnet GBC are examples of potentially useful compounds.

Additionally ultraviolet absorbers that may be desirable include those selected from hydroxybenzophenones, hydroxyphenylbenzotriazoles and formamidines. The absorbers may be used alone or in combination to achieve the spectral sensitivity characteristics that are desired.

Representative examples of useful hydroxybenzophenones are 2-hydroxy-4-n-octoxybenzophenone (UV-CHEK AM-300 from Ferro Chemical Division, Mark 1413 from Argus Chemical Division, Witco Chem. Corp., and Cyasorb UV-531 Light Absorber from American Cyanamid), 4-dodecyl-2-hydroxybenzophenone (Eastman Inhibitor DOBP from Eastman Kodak), 2-hydroxy-4-methoxybenzophenone (Cyasorb UV-9 Light Absorber from American Cyanamid), and 2,2'-dihydroxy-4-methoxybenzophenone (Cyasorb UV-24 Light Absorber from American Cyanamid). Representative examples of useful hydroxybenzophenyl benzotriazoles are 2-(2'-hydroxy-5'-methylphenyl)benzotriazole (Tinuvin P from Ciba-Geigy Additives Dept.), 2-(3',5'-ditert-butyl-2'hydroxyphenyl)-5-chlorobenzotriazole (Tinuvin 327 from Ciba-Geigy), and 2-(2-hydroxy-5-t-octylphenyl)benzotriazole (Cyasorb UV-5411 Light Absorber from American Cyanarnid). Representative examples of useful formamidines are described in U.S. Pat. No. 4,021,471 and include N-(p-ethoxy-carbonylphenyl)-N-ethyl-N-phenylfounamicline (Givsorb UV-2 from Givaudan Corp.). The optimum absorber and concentration of absorber for a particular application depends on both the absorption maximum and extinction coefficient of the absorber candidates and the spectral sensitivity characteristics of the associated photoinitiators.

Additionally, the microcapsules, photosensitive compositions, image-forming agents, developers, and development techniques described in U.S. Pat. Nos. 4,399,209 and 4,440,846.

The compounds according to the present invention are also particularly effective against powdery mildews and rusts, pyrenophora, rhynchosporium, tapesia, fusarium and leptosphaeria fungi, in particular against pathogens of monocotyledonous plants such as cereals, including wheat and barley. They are furthermore particularly effective against downy mildew species, powdery mildews, leaf spot diseases and rusts in dicotyledonous plants.

The amount of the compounds of the invention to be applied, will depend on various factors such as the compound employed, the subject of the treatment (substrate), the type of treatment (e.g., spraying, dusting, seed dressing), the purpose of the treatment (prophylactic or therapeutic), the type of fungi and/or bacteria to be treated and the application time.

The agents may be applied before or after infection of any of the materials listed by the fungi and/or bacteria.

When applied to the plants, the compounds described herein are applied at a rate of 25 to 250 g/ha, generally from 50 to 150 g/ha, e.g., 75, 100, 125 or 150 g/ha, in association with 20 to 2000 g/ha, generally from 20 to 1000 g/ha.

In industrial practice the application rates of the combination depend on the type of effect desired, and range from 0.02 to 3 kg of active ingredient per hectare.

When the active ingredients are used for treating seed, rates of 0.001 to 50 g a.i. per kg, and generally from 0.01 to 10 g per kg of seed are generally sufficient.

The composition of the invention can be employed in any conventional form, for example in the form of a twin pack, an instant granulate, a flowable formulation, an emulsion concentrate or a wettable powder in combination with industrially acceptable adjuvants, including surfactants such as sodium lauryl sulfate. Such compositions may be produced in conventional manner, e.g., by mixing the active ingredients with appropriate adjuvants (diluents or solvents and optionally other formulating ingredients such as surfactants). Also conventional slow release formulations may be employed where long lasting efficacy is intended.

Particular formulations to be applied in spraying forms such as water dispersible concentrates or wettable powders may contain surfactants such as wetting and dispersing agents, e.g., the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g., as slow release capsules or microcapsules.

In general, the formulations include from 0.01 to 90% by weight of active agent, from 0 to 20% industrially acceptable surfactant and 10 to 99.99% solid or liquid adjuvant(s), the active agent consisting of at least a compound described hererin, and optionally other active agents, particularly microbides or conservatives or the like. Concentrated forms of compositions generally contain in between 2 and 80%, generally from between 5 and 70% by weight of active agent. Application forms of formulation may for example contain from 0.01 to 20% by weight, generally from 0.01 to 5% by weight of active agent. Whereas commercial products will generally be formulated as concentrates, the end user will normally employ dilute formulations.

Additionally, the color of the present compounds may be removed by a type of "bleaching." Furthermore, it has been found possible to bleach the colored substances leached from the present compound in dyed textiles and building materials or from textiles and building materials soiled with a colorant in a solution of wash liquor thereby preventing the colored substance in question from being deposited on other textiles and building materials in the wash liquor, when enzymes utilizing hydrogen peroxide or molecular oxygen for the oxidation of organic or inorganic substances, including colored substances, are added to the wash liquor. Such enzymes are usually termed peroxidases and oxidases, respectively. It is well recognized in the art (cf. for instance B. C. Saunders et al., Peroxidase, London, 1964, p. 10 ff.) that peroxidases act on various amino and phenolic compounds resulting in the production of a color. In view of this, it must be considered surprising that peroxidases (and certain oxidases) may also exert an effect on colored substances in solution such that dye transfer is inhibited. While the mechanism governing the ability of these enzymes to effect dye transfer inhibition has not yet been elucidated, it is currently believed that the enzymes act by reducing hydrogen peroxide or molecular oxygen and oxidizing the colored substance (donor substrate) dissolved or dispersed in the wash liquor, thereby either generating a colorless substance or providing a substance which is not adsorbed to the fabric or building material.

Additionally, a liquid composition of matter according to the present invention may be focused and may be mixed with and/or diluted by an excipient. When the excipient serves as a diluent, it may be a solid, semi-solid, or liquid material that acts as a vehicle, carrier, or medium for the composition of matter. Various suitable excipients will be understood by those skilled in the art and may be found in the *National*

*Formulary*, 19: 2404-2406 (2000), the disclosure of pages 2404 to 2406 being incorporated by reference herein in their entirety. Preferable excipients include butanedioal and EDTA. Examples of suitable excipients include, but are not limited to, starches, gum arabic, calcium silicate, microcrystalline cellulose, methacrylates, shellac, polyvinylpyrrolidone, cellulose, water, syrup, and methylcellulose. An aqueous medium may include an active ingredient or ingredients, a quantity of one or more surfactants sufficient to dissolve or suspend said active ingredients uniformly throughout the medium and other manufacturing additives as known to the art. The latter include granulating-binding agents such as gelatin; natural gums, such as acacia, tragacanth; starches, sodium alginate, sugars, polyvinylpyrrolidone; cellulose derivatives such as hydroxypropylmethylcellulose, polyvinyloxoazolidones; pharmaceutical fillers such as lactose, microcrystalline cellulose, dicalcium phosphate, tricalcium phosphate, calcium sulfate, dextrose, mannitol, sucrose; tabletting lubricants if needed such as calcium and magnesium stearate, stearic acid, talc, sterotex (alkaline stearate). The term "aqueous medium" for one ingredient of one of the embodiments of the invention is used within the custom of the art. Primarily, it connotes a water medium, with added water-miscible solvents such as isopropanol or ethanol when needed, to support the active ingredient.

Pharmaceutical Compositions

Additionally, the present invention provides a method for the prophylaxis or treatment of a condition or disorder as described herein in a mammal, such as a human, which includes administration of a therapeutically effective amount of a compound described herein, or a pharmaceutically-acceptable solvate thereof.

In particular, the present invention provides compounds described herein, or a pharmaceutically acceptable solvate thereof for use in medical therapy; particularly, for use in the prophylaxis or treatment of an inflammatory condition, allergic condition or immune disorder in a mammal, such as a human.

Thus, in another aspect of the present invention, there are provided pharmaceutical compositions including, as active ingredients, compounds described herein or a pharmaceutically acceptable salt or solvate thereof, together with at least one pharmaceutical carrier or excipient. These pharmaceutical compositions may be used in the prophylaxis and treatment of inflammatory conditions, allergic conditions, infectious conditions, and immune disorders. The carrier must be pharmaceutically acceptable to the recipient and must be compatible with, i.e., not have a deleterious effect upon, the other ingredients in the composition. The carrier may be a solid or liquid and is preferably formulated as a unit dose formulation, for example, a tablet which may contain from 0.05 to 95% by weight of the active ingredients. If desired other physiologically active ingredients—may also be incorporated in the pharmaceutical compositions of the invention.

The pharmaceutical compositions according to embodiments of the present invention include those suitable for oral, rectal, topical, nasal, inhalation (e.g., via an aerosol) buccal (e.g., sub-lingual), vaginal, topical (i.e., both skin and mucosal surfaces, including airway surfaces), transdermal administration and parenteral (e.g., subcutaneous, intramuscular, intradermal, intraarticular, intrapleural, intraperitoneal, intrathecal, intracerebral, intracranially, intraarterial, or intravenous), although the most suitable route in any given case will depend on the nature and severity of the condition being treated and on the nature of the particular active agent which is being used.

Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions.

Formulations suitable for sublingual or buccal administration include lozenges comprising the active compound and, typically a flavored base, such as sugar and acacia or tragacanth and pastilles comprising the active compound in an inert base, such as gelatin and glycerin or sucrose acacia.

Formulations suitable for rectal administration are preferably provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols and oils. Suitable carriers for such formulations include petroleum jelly, lanolin, polyethylene glycols, alcohols, DMSO and combinations thereof. The active ingredient is typically present in such formulations at a concentration of from 0.1 to 15% w/w.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent.

Aqueous solutions are typically prepared by dissolving the active ingredient in saline to which cyclodextrin has been added.

Suitable formulations for administration by inhalation include fine particle dusts or mists which may be generated by means of various types of metered dose pressurized aerosols, nebulisers, or insufflators.

For pulmonary administration via the mouth, the particle size of the powder or droplets is typically in the range 0.5-10 µm, preferably 1-5 µm, to ensure delivery into the bronchial tree. For nasal administration, a particle size in the range 10-500 µm is preferred to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 µl, to produce a fine particle spray containing the active ingredient. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol as well as fatty acid surfactants, such as oleic acid or sorbitan trioleate, anti-oxidants and suitable flavouring agents.

Nebulisers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulisers consist of the active ingredient in a liquid carrier and comprising up to 40% w/w of the formulation, preferably less than 20% w/w. The carrier is typically water or a dilute aqueous alcoholic solution, preferably, made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100 w/w of the formulation.

Therefore, according to a further aspect of the present invention, there is provided the use of a compound described herein or a pharmaceutically acceptable solvate thereof in the preparation of a medicament for the prophylaxis or treatment of a condition or disorder described therein.

The extent of pegylation can be modified to provide a desirable formulation, i.e., liquid, gel, hard, soft, etc.

Suitable Subjects

Subjects suitable to be treated for non-industrial purposes include, but are not limited to, plant, avian and mammalian subjects. Mammals of the present invention include, but are not limited to, canines, felines, bovines, caprines, equines, ovines, porcines, rodents (e.g., rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

In therapeutic use for treatment of conditions in mammals (i.e. humans or animals) for which the compounds of the present invention or an appropriate pharmaceutical composition thereof are effective, the compounds of the present invention may be administered in an effective amount. Since the activity of the compounds and the degree of the therapeutic effect vary, the actual dosage administered will be determined based upon generally recognized factors such as age, condition of the subject, route of delivery and body weight of the subject. The dosage can be from about 0.1 to about 100 mg/kg, administered orally 1 to 4 times per day.

The amount of a compounds described herein or pharmaceutically acceptable salt or solvate thereof, which is required to achieve the desired biological effect will depend on a number of factors such as the use for which it is intended, the means of administration, and the recipient. A typical daily dose may be expected to lie in the range of 0.005 mg/kg-100 mg/kg, preferably 0.05-50 mg/kg, and most preferably 0.5-20 mg/kg. This dose may be administered as a single unit dose or as several separate unit doses or as a continuous infusion. An intravenous dose may be expected to lie in the range of 0.0025 mg/kg to 50 mg/kg and would typically be administered as an infusion. Similar dosages would be applicable for the treatment of various disease states. For administration to the lungs of a subject by aerosol an amount of the compound should be used sufficient to achieve concentrations on the airway surface liquid of the subject of about 2 to 1000 μmol.

The present invention is explained in greater detail in the Examples, including schemes, that follow. These examples are intended as illustrative of the invention and are not to be taken are limiting thereof.

EXAMPLE 1

Synthesis of 1-[ω-Methoxypoly(ethylene gylcol)]ethyl-(E,E)-2,6-bis[2-[4-(pyrrolidinyl)phenyl]ethenyl]Pyridinium Mesylate Synthesis of 1-[ω-methoxypoly(ethylene glycol)]ethyl-(E, E)-2,6-bis[2-[4-(pyrrolidinyl)phenyl]ethenyl]pyridinium mesylate,also known as 2,6-bis-[2-[4-(N-pyrrolidino)phenyl]vinyl]-1-[methoxy(polyethyleneoxy)$_{n-1}$]-ethyl pyridinium methanesulfonate (or "mPEG750-stilbazium mesylate"), where n is from 15 to 17 and X is OMs, was carried out as described below and in accordance with Scheme 2 below.

A solution of 10 mmol of lutidine (1) and 1 mmol of ω-methoxy-1-mesylpoly(ethylene glycol) (ave. molecular weight 750 Daltons), also known as MeO-PEG750-OMs (2a, Biolink Life Sciences, Inc., Cary, N.C.) was heated at 115° C. for 72 hours. The reaction mixture was cooled to ambient temperature, and the oily residue that formed was washed successively with hexanes, methyl t-butyl ether and tetrahydrofuran. Thin layer chromatographic analysis (silica gel G eluted with 10% methanol in chloroform) of a solution of the residue in methanol indicated formation of the pyridinium salt. The NMR spectrum was difficult to analyze but supported the identification of the product as 2,6-dimethyl-N-[ω-methoxypoly(ethylene glycol)]ethylpyridinium mesylate (3), the desired product. This intermediate is also named N-[methoxy(polyethyleneoxy)$_{n-1}$]ethyl 2,6-lutidinium mesylate (3) where n is in the 15-17 range and X is OMs. A slurry of this pyridinium mesylate 3 obtained accordingly to the previously described methods (0.86 mmol; 1 eq.), 4-pyrrolylbenzaldehyde (4) (2.1 mmol; 2.5 eq.), and piperidine (1.3 mmol; 1.5 eq.) in benzene was heated at 80° C. overnight. The reaction mixture was cooled to room temperature, and the solvent was decanted from the dark maroon solid that formed. The solid was washed successively with hexanes and methyl t-butyl ether. The $^1$H NMR spectrum supported the identification of the product as a methoxyPEGylated pyridinium compound also known as 2,6-bis-[2-[4-(N-pyrrolidino)phenyl]vinyl]-1-[methoxy(polyethyleneoxy)$_{n-1}$]-ethyl pyridinium methanesulfonate (or "mPEG750-stilbazinm mesylate")—(5, X is OMs). The product could be readily dissolved in water to give a dark maroon solution. See FIG. 1.

EXAMPLE 2

N-[Methoxy(polyethyleneoxy)$_{n-1}$]ethyl 2,6-Lutidinium Methanesulfonate (mPEG750-ethyl lutidinium mesylate)

By several variations of temperature (room temperature to reflux) and time differences (days to weeks) from Example 1, commercially available 2,6-lutidine (1) was successfully reacted with MeO-PEG750-OMs (2a (5), Biolink Life Sciences, Inc., Cary, N.C.) to yield N-[methoxy(polyethyleneoxy)$_{n-1}$]ethyl 2,6-lutidinium mesylate (3) where n is from 15 to 17 and X is OMs.

EXAMPLE 3

N-[Methoxy(polyethyleneoxy)$_{n-1}$]ethyl 2,6-Lutidinium p-Toluenesulfonate (mPEG350-ethyl lutidinium tosylate)

In a similar manner to Example 1 and Example 2, commercially available 2,6-lutidine (1) can be reacted with MeO-PEG350-OTs (6, Biolink Life Sciences, Inc., Cary, N.C. BLS-107-350) to yield N-[methoxy(polyethyleneoxy)$_{n-1}$]ethyl 2,6-lutidinium tosylate (3) where n is from 7 to 8 and X is OTs.

EXAMPLE 4

N-[Methoxy(polyethyleneoxy)$_{n-1}$]ethyl 2 6-Lutidinium Chloride (mPEG1000-ethyl lutidinium chloride)

In a similar manner to Example 1 and Example 2, commercially available 2,6-lutidine (1) can be reacted with MeO-PEG1000-Cl (7, Biolink Life Sciences, Inc., Cary, N.C. BLS-106-1000) to yield N-[methoxy(polyethyleneoxy)$_{n-1}$]ethyl 2,6-lutidinium chloride (3) where n is from 19 to 24 and X is Cl.

EXAMPLE 5

2,6-Bis-[2-[4-(N-pyrrolidino)phenyl]vinyl]-1-[methoxy(polyethyleneoxy)$_{n-1}$]-ethyl Pyridinium Methanesulfonate (mPEG750-stilbazium mesylate)

A sample of methoxy(polyethyleneoxy)$_{n-1}$-ethyl lutidinium mesylate (3, X is OMs) was reacted with commercially available 4-(N-pyrrolidino)benzaldehyde (4) in heated ethanol containing a catalytic amount of piperidine to yield 2,6-bis-[2-[4-(N-pyrrolidino)phenyl]vinyl]-1-[methoxy(polyethyleneoxy)$_{n-1}$]-ethyl pyridinium methanesulfonate (5, X is OMs)) where n is from 15 to 17 and X is OMs.

EXAMPLE 6

2,6-Bis-[2-[4-(N-pyrrolidino)phenyl]-vinyl]-1-[methoxy(polyethyleneoxy)$_{n-1}$]-ethyl Pyridinium p-Toluenesulfonate (mPEG350-stilbazium tosylate)

In a similar manner to Example 5, a sample of methoxy(polyethyleneoxy)$_{n-1}$-ethyl lutidinium tosylate (3, X is OTs) can be reacted with commercially available 4-(N-pyrrolidino)benzaldehyde (4) in heated ethanol containing a catalytic amount of piperidine to yield 2,6-bis-[2-[4-(N-pyrrolidino)phenyl]vinyl]-1-[methoxy(polyethyleneoxy)$_{n-1}$]-ethyl pyridinium p-toluenesulfonate (5, X is OTs) where n is from 7 to 8.

EXAMPLE 7

2,6-Bis-[2-[4-(N-pyrrolidino)phenyl]vinyl]-1-[methoxy(polyethyleneoxy)$_{n-1}$]-ethyl Pyridinium Chloride (mPEG1000-stilbazium chloride)

In a similar manner to Example 5, a sample of methoxy(polyethyleneoxy)$_{n-1}$-ethyl lutidinium chloride (2, X is Cl) can be reacted with commercially available 4-(N-pyrrolidino)benzaldehyde (4) in heated ethanol containing a catalytic amount of piperidine to yield 2,6-bis-[2-[4-(N-pyrrolidino)phenyl]vinyl]-1-[methoxy(polyethyleneoxy)$_{n-1}$]-ethyl pyridinium chloride (5, X is Cl)) where n is from 19 to 24.

EXAMPLE 8

Physiochemical Properties of Exemplary Pegylated Pyridinium Compounds

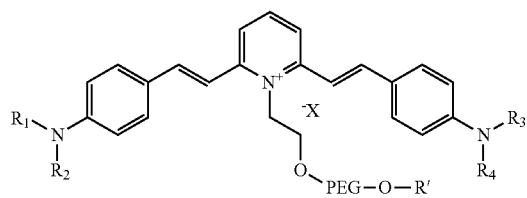

R' is H, CH$_3$, C$_2$H$_5$ and CH$_3$CO

EXAMPLE 9

Synthesis Scheme for Exemplary Pegylated Pyridinium Compounds

Schemes 2 and 3 below describe illustrative synthetic methods for exemplary pegylated pyridinium compounds of the present invention and complement the examples presented above.

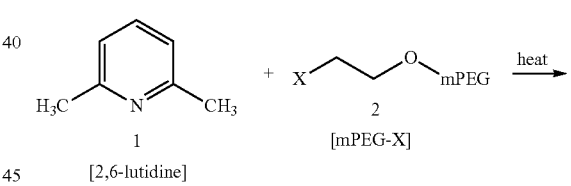

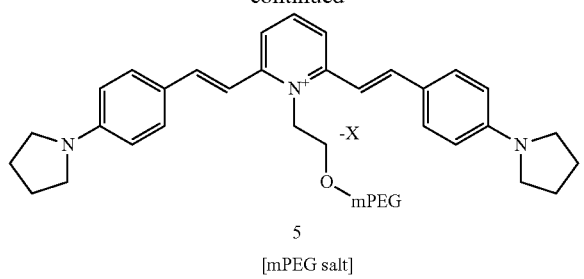

5

[mPEG salt]

Scheme 3

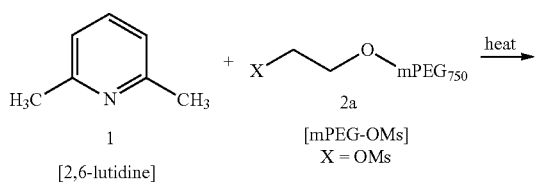

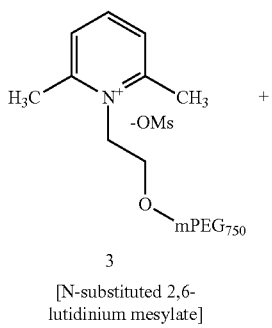

3

[N-substituted 2,6-lutidinium mesylate]

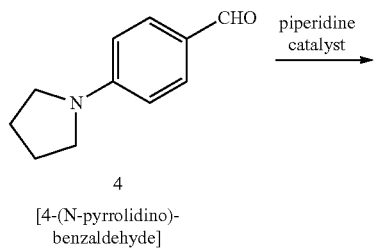

4

[4-(N-pyrrolidino)-benzaldehyde]

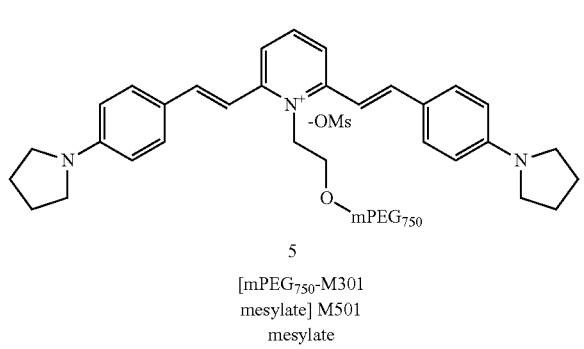

5

[mPEG750-M301 mesylate] M501 mesylate

EXAMPLE 10

4-(4-cyclohexylphenyl)-2-(N,N-diethylaminostyryl)-3-[methoxy(polyethylene)$_{n-1}$]Ethylthiazolium Chloride (4-(4-cyclohexylphenyl)-2-[2-(4-dimethylaminophenyl)vinyl]-3-[methoxy(polyethylene)$_{n-1}$]ethylthiazol-3-ium chloride)

p-cyclohexylphenyl methyl ketone is reacted with bromine in a non-polar solvent to produce the corresponding p-cyclohexylphenacyl bromide. Reaction of this reactive alpha-bromo ketone with commercially available thioacetamide in an protic solvent such as methanol with heat affords the corresponding 2-methyl-4-(4-cyclohexylphenylthiazole. N-Alkylation of this thiazole with [methoxy(polyethylene)$_{n-1}$]ethyl chloride (where n is from 19 to 24) in aprotic solvents such as dimethylformamide and heat readily forms the corresponding methochioride product, which is also named either N-[methoxy(polyethylene)$_{n-1}$]ethyl-2-methyl-4-(4-cyclohexylphenypthiazolium chloride or 3-[methoxy(polyethylene)$_{n-1}$]ethyl-2-methyl-4-(4-cyclohexylphenyl)thiazolium chloride. Reaction of this thiazolium chloride with (N,N-dimethyl)amino benzaldehyde in a protic solvent such as methanol with a basic catalyst such as piperidine and heat then produces the desired 4-(4-cyclohexylphenyl)-2-(N,N-diethylaminostyryl)-3-[methoxy(polyethylene)$_{n-1}$]ethylthiazolinm chloride, which can also be named 4-(4-cyclohexylphenyl)-2-[2-(4-dimethylaminophenyl)vinyl]-3-[methoxy(polyethylene)$_{n-1}$]ethylthiazol-3-ium chloride. In all of the above reactions n is from 19 to 24.

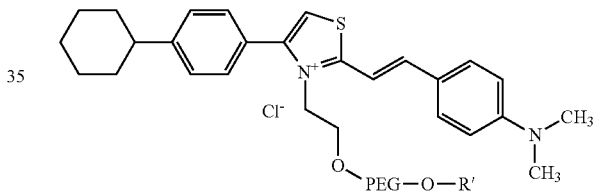

2-(N,N-dimethylstyryl)-4-cyclohexylphenyl-3-[methoxy(polyethyleneoxy)n-1]-ethylthiazolium chloride—where n is in the 19-24 range and is methyl The foregoing is illustrative of the present invention, and is not to be construed as limiting thereof. The invention is defined by the following claims, with equivalents of the claims to be included therein.

What is claimed is:

1. A compound comprising the following structure:

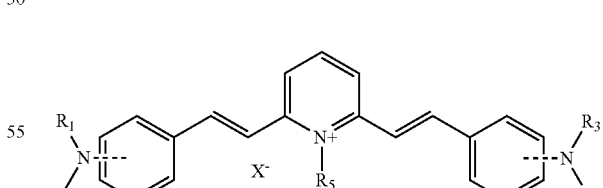

or a solvate thereof, wherein
NR$_1$R$_2$ and NR$_3$R$_4$ are in the ortho, meta or para positions;
X$^-$ is an anionic salt;
R$_1$, R$_2$, R$_3$, or R$_4$ are the same or different and independently selected from the group consisting of C$_{1-10}$ alkyl (linear or branched) and alkenes (linear or branched), or wherein R$_1$ and R$_2$ or R$_3$ and R$_4$ taken together with the nitrogen atom to which they are attached form pyrrolidino or piperidino rings; and $R_5$ is a polyalkylene glycol moiety comprising a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol.

2. The compound of claim 1, wherein $X^-$ is fluoride, chloride, bromide, iodide, halide, methanesulfonate (mesylate), p-toluenesulfonate (tosylate), napthylate, m-nitrobenzenesulfonate (nosylate), para-aminobenzoate, lauryl sulfate, 2,4-dihydroxy benzophenone, 2-(2-hydroxy-5'-methylphenyl)benzotriazole or benzenesulfonate (besylate).

3. The compound of claim 1, wherein $R_5$ is a polyalkylene glycol moiety comprising a $C_{1-5}$ alkyl (linear or branched) substituted polyethylene glycol.

4. The compound of claim 1, wherein the compound is 2,6-bis-[2-[4-(N-pyrrolidino)phenyl]vinyl]-1-[methoxy(polyethyleneoxy)$_{n-1}$]-ethyl pyridinium p-toluenesulfonate (mPEG350-stilbazium tosylate); 2,6-bis-[2-[4-(N-pyrrolidino)phenyl]vinyl]-1-[methoxy(polyethyleneoxy)$_{n-1}$]-ethyl pyridinium methanesulfonate (mPEG750-stilbazium mesylate); 2,6-bis-[2-[4-(N-pyrrolidino)phenyl]vinyl]-1-[methoxy(polyethyleneoxy)$_{n-1}$]-ethyl pyridinium chloride (mPEG1000-stilbazium chloride); 2,6-bis-[2-[4-(N-pyrrolidino)phenyl]vinyl]-1-[methoxy(polyethyleneoxy)$_{n-1}$]-ethyl pyridinium iodide (mPEG1000-stilbazium iodide); 2,6-bis-[2-[4-(N,N-dimethylamino)phenyl]vinyl]-1-[methoxy(polyethyleneoxy)$_{n-1}$]-ethyl pyridinium p-toluenesulfonate, wherein n is from 7 to 8 and X is OTs; 2,6-bis-[2-[4-(N,N-dimethylamino)phenyl]vinyl]-1-[methoxy(polyethyleneoxy)$_{n-1}$]-ethyl pyridinium methanesulfonate, wherein n is from 15 to 17 range and X is OMs; 2,6-bis-[2-[4-(N,N-dimethylamino)phenyl]vinyl]-1-[methoxy(polyethyleneoxy)$_{n-1}$]-ethyl pyridinium chloride, wherein n is from 19 to 24 and X is Cl.

5. The compound of claim 1, wherein the compound has the following structure:

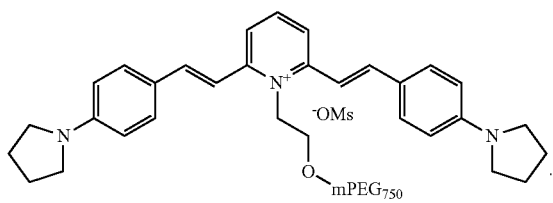

6. The compound of claim 1, wherein the compound has the following structure:

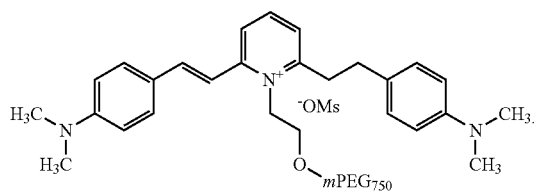

7. A compound comprising the following structure:

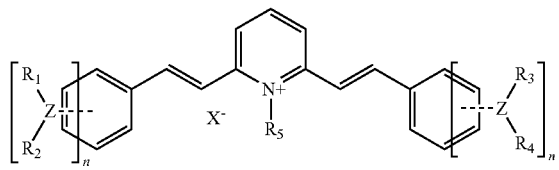

or a solvate thereof, wherein n is a number from 1 to 5;

Z is C, N, O, S or a halogen;

$ZR_1R_2$ and $ZR_3R_4$ are in the ortho, meta or para positions;

$X^{31}$ is an anionic salt;

$R_1$, $R_2$, $R_3$, or $R_4$ are the same or different and independently selected from the group consisting of $C_{1-10}$ alkyl (linear or branched) and alkenes (linear or branched), or wherein $R_1$ and $R_2$ or $R_3$ and $R_4$ taken together with the nitrogen atom to which they are attached form pyrrolidino or piperidino rings; and $R_5$ is a polyalkylene glycol moiety comprising a $C_{1-5}$ alkyl (linear or branched) substituted polyethylene glycol, a $C_{2-5}$ alkene (linear or branched) substituted polyethylene glycol or a $C_{2-5}$ alkyne substituted polyethylene glycol.

8. The compound of claim 7, wherein the compound is in an E, E configuration.

9. A composition comprising:
(a) a compound of claim 1; and
(b) a pharmaceutically, agriculturally or industrially acceptable carrier, excipient or diluent.

10. The composition of claim 9, further comprising an antimicrobial agent.

11. The composition of claim 9, further comprising an insecticide.

12. A method of treating an industrial product having a microbial growth, comprising administering to the site of the product where growth is to be treated an effective amount of a compound of claim 1.

13. The method of claim 12, wherein the industrial product is wood, air ducts, lumber, decks, buoys, seawalls, retaining walls, docks, pilings, watercrafts, boats, pipes, stucco, tiles, paint, insulation, roofs, roofing materials, building materials, metal, concrete and cement based materials, plasters, asphalts, ceramics, stucco, grout, plastics, glass, computer parts, food packaging, swimming pools, pool surfaces, hot tubs, spas, wall coverings, siding materials, flooring, filtration systems, cooling towers and/or substrates.

14. A method of treating an infection, an allergic condition, inflammation or an immune disorder, in a subject, comprising administering a composition comprising a compound of claim 1.

15. A method of protecting a plant from fungal infection, comprising contacting a plant during a stage of the growth of the plant with a compound of claim 1.

* * * * *